United States Patent
Shaker et al.

(10) Patent No.: US 10,582,932 B2
(45) Date of Patent: Mar. 10, 2020

(54) SWALLOW EXERCISER

(71) Applicants: THE MEDICAL COLLEGE OF WISCONSIN, INC., Milwaukee, WI (US); UNIVERSITY OF SOUTHERN CALIFORNIA, Los Angeles, CA (US)

(72) Inventors: Reza Shaker, Brookfield, WI (US); Anisa Shaker, Los Angeles, CA (US)

(73) Assignees: The Medical College of Wisconsin, Milwaukee, WI (US); University of Southern California, Los Angeles, CA (US)

( * ) Notice: Subject to any disclaimer, the term of this patent is extended or adjusted under 35 U.S.C. 154(b) by 0 days.

(21) Appl. No.: 15/502,925

(22) PCT Filed: Aug. 11, 2015

(86) PCT No.: PCT/US2015/044634
§ 371 (c)(1),
(2) Date: Feb. 9, 2017

(87) PCT Pub. No.: WO2016/025466
PCT Pub. Date: Feb. 18, 2016

(65) Prior Publication Data
US 2017/0237456 A1 Aug. 17, 2017

Related U.S. Application Data

(60) Provisional application No. 62/035,670, filed on Aug. 11, 2014.

(51) Int. Cl.
*A61B 17/132* (2006.01)
*A61B 17/135* (2006.01)
(Continued)

(52) U.S. Cl.
CPC ........ *A61B 17/1327* (2013.01); *A61B 17/132* (2013.01); *A61B 17/135* (2013.01);
(Continued)

(58) Field of Classification Search
CPC . A61B 17/1325; A61B 17/12; A61B 17/1327; A61B 17/135;
(Continued)

(56) References Cited

U.S. PATENT DOCUMENTS 3,164,151 A * 1/1965 Vere Nicoll ............ A61F 5/012
128/DIG. 23
4,718,662 A 1/1988 North
(Continued)

FOREIGN PATENT DOCUMENTS

CA 2807044 A1 11/2006
CA 2624164 A1 3/2008
(Continued)

OTHER PUBLICATIONS

Abstract of JP 2001170120, published Jun. 26, 2001.
(Continued)

*Primary Examiner* — George J Ulsh
(74) *Attorney, Agent, or Firm* — Quarles & Brady LLP

(57) ABSTRACT

A swallow exerciser device that exercises and thereby strengthens the muscles involved in swallowing includes a rigid shell, an adjustable fastener, and an inflatable pad. The rigid shell has a longitudinal dimension such that the shell extends above and below the larynx of the subject when the swallow exerciser device is positioned over the larynx of the subject. The adjustable fastener is dimensioned to secure the shell around a neck of the subject with the shell positioned over the larynx of the subject. The inflatable pad is connected to a proximal surface of the shell. The inflatable pad is dimensioned to apply resistance to force of at least one
(Continued)

swallowing muscle of the subject when the shell positioned over the larynx of the subject and when the inflatable pad is in an inflated position. The swallow exerciser device can be used in a method for improving swallowing function in a subject.

37 Claims, 23 Drawing Sheets

(51) Int. Cl.
  *A61B 17/00* (2006.01)
  *A61B 90/00* (2016.01)
(52) U.S. Cl.
  CPC .............. *A61B 2017/00827* (2013.01); *A61B 2090/065* (2016.02)
(58) Field of Classification Search
  CPC .... A61B 2017/00827; A61B 2090/065; A61B 17/1322; A61F 5/055
  See application file for complete search history.

(56) References Cited

U.S. PATENT DOCUMENTS

| | | | |
|---|---|---|---|
| 5,143,087 | A | 9/1992 | Yarkony |
| 5,213,553 | A | 5/1993 | Light |
| 5,403,266 | A * | 4/1995 | Bragg ..................... A61F 5/012 602/13 |
| 5,483,974 | A | 1/1996 | Crangle |
| 6,702,765 | B2 | 3/2004 | Robbins |
| 7,238,145 | B2 | 7/2007 | Robbins |
| 8,388,561 | B2 | 3/2013 | Ludlow |
| 8,583,240 | B2 | 11/2013 | Freed |
| 9,351,737 | B1 * | 5/2016 | Carmichael .......... A61B 17/135 |
| 2003/0229375 | A1 | 12/2003 | Fleischer |
| 2010/0049103 | A1 | 2/2010 | Ludlow et al. |
| 2012/0252633 | A1 | 10/2012 | Valakh |
| 2013/0090573 | A1 | 4/2013 | Shaker |
| 2013/0110019 | A1 * | 5/2013 | Hopman .............. A61B 17/135 602/13 |
| 2013/0177885 | A1 | 7/2013 | Kirkpatrick |
| 2013/0338551 | A1 | 12/2013 | Ludlow |
| 2015/0209052 | A1 * | 7/2015 | Hopman ............ A61B 17/1325 606/203 |
| 2016/0095605 | A1 * | 4/2016 | Maris ................. A61B 17/1325 606/201 |

FOREIGN PATENT DOCUMENTS

| | | |
|---|---|---|
| CN | 101518475 B | 9/2009 |
| EP | 2178435 | 4/2010 |
| EP | 2381835 A1 | 11/2011 |
| GB | 2405088 A | 2/2005 |
| JP | 2001170120 | 6/2001 |
| JP | 2008544832 A | 12/2008 |
| JP | 2014042835 A | 3/2014 |
| WO | 1997015349 | 5/1997 |
| WO | 1999/003440 | 1/1999 |
| WO | 2006062746 A2 | 6/2006 |
| WO | 2008094581 A2 | 8/2008 |
| WO | 2010062292 | 6/2010 |
| WO | 2011156064 | 12/2011 |
| WO | 2014186500 A2 | 11/2014 |

OTHER PUBLICATIONS

Machine translation of JP 2001-170120.
R. Shaker et al., Effects of Laryngeal Restriction on Pharyngeal Peristalsis and Biomechanics: Clinical Implications; 310 Am. J. Physiol Gastrointest Liver Physiol; G1036-G1043 (2016).
R. Shaker et al., Rehabilitation of Swallowing by Exercise in Tube-Fed Patients with Pharyngeal Dysphagia Secondary to Abnormal UES Opening; 122 Gastroenterology; 1314-1321 (2002).
The International Search Report and Written Opinion dated Feb. 19, 2016 for International Application No. PCT/US2015/044634.
Barikroo, Ali, et al. "Effects of age and bolus volume on velocity of hyolaryngeal excursion in healthy adults." Dysphagia 30.5 (2015): 558-564.
Ghosh, Sudip K., et al. "Physiology of the esophageal pressure transition zone: separate contraction waves above and below." American Journal of Physiology-Gastrointestinal and Liver Physiology 290.3 (2006): G568-G576.
US Statutory Invention Registration, registration No. H1557, Joubert et al., Swallowing Rehabilitation, published Jul. 2, 1996.
Jaradeh, S.. "Muscle disorders affecting oral and pharyngeal swallowing." GI Motility online (2006). Accessed online at https://www.nature.com/gimo/contents/pt1/full/gimo35.html on Jul. 2, 2019.
Kern, Mark, et al. "Comparison of upper esophageal sphincter opening in healthy asymptomatic young and elderly volunteers." Annals of Otology, Rhinology & Laryngology 108.10 (1999): 982-989.
Kim, Y. et al. "Maximal hyoid excursion in poststroke patients." Dysphagia 25.1 (2010): 20-25.
Lang, I. M. "Upper esophageal sphincter." GI Motility online (2006). Accessed online at https://www.nature.com/gimo/contents/pt1/full/gimo12.html.
Lin, Z., et al. "Automated calculation of the distal contractile integral in esophageal pressure topography with a region-growing algorithm." Neurogastroenterology & Motility 24.1 (2012): e4-e10.
Paik, Nam-Jong, et al. "Movement of the hyoid bone and the epiglottis during swallowing in patients with dysphagia from different etiologies." Journal of Electromyography and Kinesiology 18.2 (2008): 329-335.
Yokoyama, Masato, et al. "Role of laryngeal movement and effect of aging on swallowing pressure in the pharynx and upper esophageal sphincter." The Laryngoscope 110.3 (2000): 434-439.
Shaker, R., et al. "Augmentation of deglutitive upper esophageal sphincter opening in the elderly by exercise." American Journal of Physiology-Gastrointestinal and Liver Physiology 272.6 (1997): G1518-G1522.

* cited by examiner

UES Margins

- Margin placed at nearest centimeter outside of resting UES 20 mmHg pressure zone.

Measuring CI

Identifying Nadir Sensor

CI Slope Compared (n=9)

CI Slope by Age - Elderly (n=6)

| | Slope | R value | Two-sided P | Power | Sig. Correlat |
|---|---|---|---|---|---|
| With | -2.244 | -0.240 | 0.0002 | 96.33% | Yes |
| Without | -0.431 | -0.041 | 0.524 | 9.26% | No |

CI Quartile

CI Quartile Condition: Age

CI Quartile Age: Condition

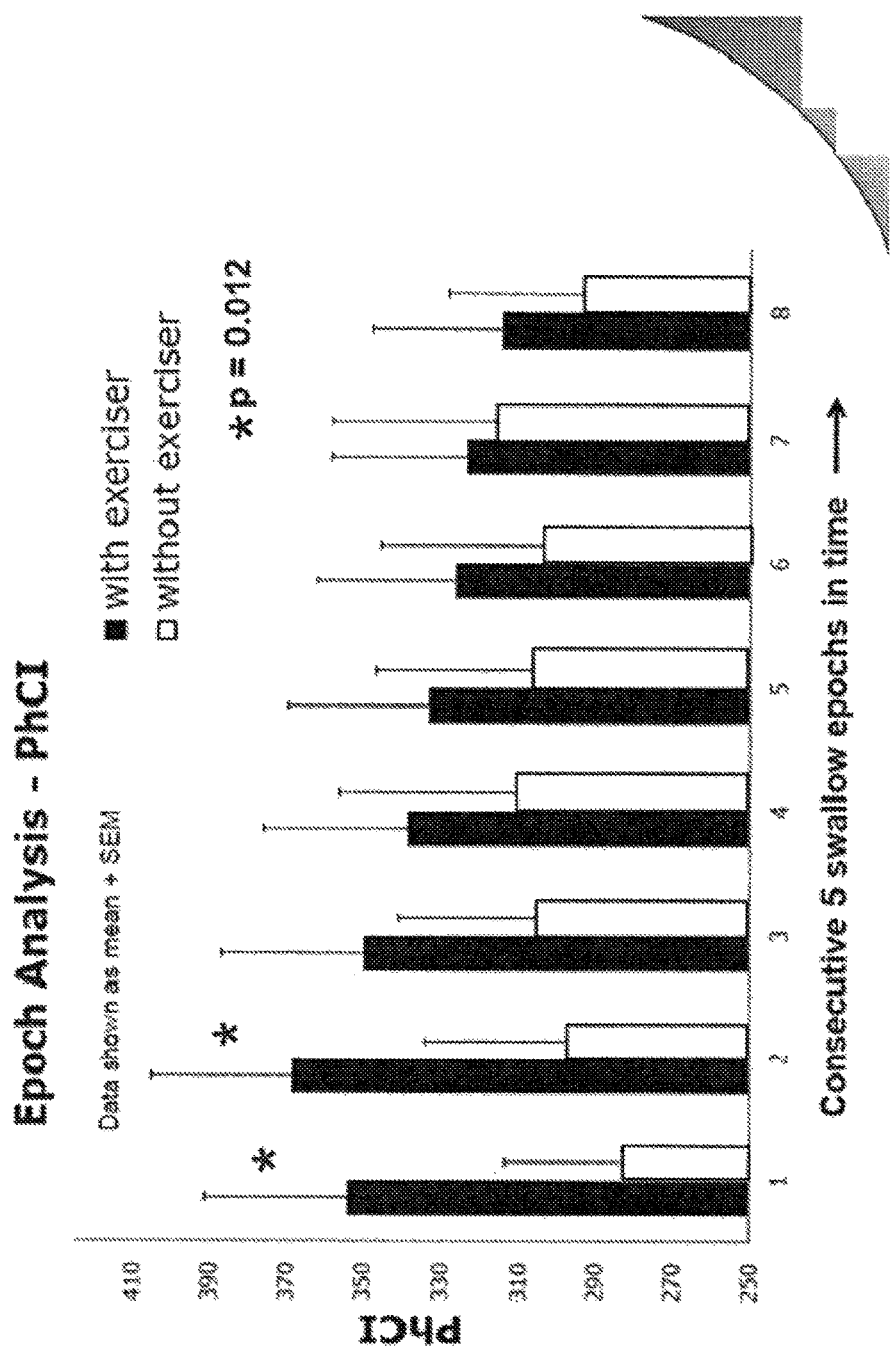

SWALLOW EXERCISER

CROSS-REFERENCE TO RELATED APPLICATIONS

This application represents the U.S. National Stage of International Application No. PCT/US2015/044634, filed Aug. 11, 2015 which claims priority from U.S. Patent Application No. 62/035,670 filed Aug. 11, 2014. The contents of this application are hereby incorporated by reference as if set forth in their entirety herein.

STATEMENT REGARDING FEDERALLY SPONSORED RESEARCH

This invention was made with government support under R01DK025731 and P01DK068051 awarded by the National Institutes of Health. The government has certain rights in the invention.

BACKGROUND OF THE INVENTION

1. Field of the Invention

This invention relates to a device and method for exercising the swallowing muscles.

2. Description of the Related Art

Swallowing is a complicated multi-stage process that involves coordinated contraction of muscles in the tongue, lips and mouth, pharynx and esophagus, throat and neck. Swallowing can be divided into three functional stages—oral, pharyngeal, and esophageal.

During the oral phase, food is processed to form a bolus of the right size and consistency for transfer. In a rapid sequence, the tongue presses against the hard palate, generating a pressure wave directed posteriorly that propels the bolus into the oropharynx. Concurrent with this action, the soft palate elevates, while the cheeks, floor of mouth, and jaw are braced. The oral phase can be considered completed when the bolus tail enters the oropharynx, at which point the posterior dorsum of the tongue remains sealed against the soft palate to prevent retrograde escape of bolus back into the oral cavity.

The pharyngeal phase, or transfer phase, requires the hyoid bone and larynx to move superior and anterior, which brings the larynx out of the path of the bolus. Several muscle groups are activated during the pharyngeal phase. Muscles of the tongue are used to seal the oral cavity, while the digastric muscle, geniohyoid, and mylohyoid of the suprahyoid muscle group work to elevate the hyoid. Additionally, the thyrohyoid muscle of the infrahyoid muscle group moves the thyroid cartilage to the base of the hyoid, consequently elevating the larynx and the upper esophageal sphincter, which is attached to the larynx, by 2 to 2.5 centimeters. Anterior movement of the larynx is a factor in the opening of the upper esophageal sphincter. Contraction of the longitudinal muscle group (palatopharyngeus, stylopharyngeus, salpingopharyngeus) elevates and shortens the pharynx. The action of the stylopharyngeus also widens the pharynx and opposes anterior movement of the posterior pharynx. The actions of these muscles elevate the larynx as well. Muscles in the pharyngeal constrictor group (superior pharyngeal constrictor muscle, middle pharyngeal constrictor muscle, inferior pharyngeal constrictor muscle) form a muscular "tunnel" and drive food into the esophagus through the already open upper esophageal sphincter, and this action is completed by pharyngeal peristaltic contraction.

Damage to or weakness in the muscles and motor control of various structures can result in difficulty in swallowing, i.e., "dysphagia". Dysphagia can also be the result of damage to sensory nerves or sensory processing from the periphery to the cortex, which can be manifest as a reduced awareness of oral or pharyngeal light "touch" and a delay in triggering the pharyngeal swallow. Swallow apraxia, or difficulty in programming motor actions during swallow, can also have a sensory component. Dysphagia may occur following stroke and traumatic brain injury, aging and after debilitating illness such as Parkinson's disease, multiple sclerosis, amyotrophic lateral sclerosis, and head, neck and esophageal cancer.

Current treatments for dysphagia focus on "strengthening" the muscles involved with swallowing "exercises". Indeed, one of the inventors is known for the Shaker Exercise which targets the suprahyoid muscles under the chin. A patient lies flat on the floor or bed and raises his/her head to look at the toes, holding this position for 60 seconds, similar to a "sit-up". Other exercises have been developed to strengthen the tongue, lips, and jaw.

U.S. Pat. No. 8,388,561 describes a device for treating a subject with dysphagia or a speech disorder. The device includes a band equipped with a vibrator that is wrapped around the neck and positioned over the larynx. Upon activation the vibrator vibrates the larynx. The device contains an automatic stimulation controller that cycles on and off to initiate and maintain vibro-tactile stimulation to induce swallowing. The device also includes a movement and or related physiological sensor for monitoring pressure or movement changes due to elevation of the subject's larynx during attempts to swallow. In this system, the patient "cues" the system immediately before he/she swallows. The system displays this cue along with the subsequent changes in pressure etc. The device of U.S. Pat. No. 8,388,561 has disadvantages, for example, the device utilizes vibratory stimulation to induce swallowing, a sensation that may be uncomfortable for patients using the device. Additionally, the vibro-tactile stimulation is used to trigger swallowing, an action not correlated with natural bodily function.

What is needed therefore is an improved device and method for exercising the swallowing muscles and thereby strengthen the muscles involved in pharyngeal phase swallowing.

SUMMARY OF THE INVENTION

In one aspect, the present invention provides a swallow exerciser device for improving swallowing function in a subject (e.g., a mammal). In one non-limiting form, the device includes a rigid outer shell, an adjustable fastener, and an inflatable conforming inner pad. The rigid shell has a longitudinal dimension such that the shell extends above a larynx of the subject and extends below the larynx of the subject when the swallow exerciser device is positioned over the larynx of the subject. The shell has a distal surface and a proximal surface. The adjustable fastener is dimensioned to secure the shell around a neck of the subject with the shell positioned over the larynx of the subject. The inflatable pad is connected to the proximal surface of the shell. The inflatable pad is dimensioned to apply resistance to force of at least one swallowing muscle of the subject when the shell is positioned over the larynx of the subject and when the inflatable pad is in an inflated position.

In one version of the swallow exerciser device, the adjustable fastener is connected to the shell. In another version of the swallow exerciser device, a spacer (e.g., a bar) is positioned between the shell and the adjustable fastener, and the spacer is attached to the shell and/or the adjustable fastener. In another version of the swallow exerciser device, the spacer is inwardly spaced from a perimeter edge of the shell.

The inflatable pad can be dimensioned to apply resistance to force of at least one muscle of the tongue of the subject when the shell is positioned over the larynx of the subject and when the inflatable pad is in the inflated position.

The inflatable pad can be dimensioned to apply resistance to force of at least one suprahyoid muscle of the subject when the shell is positioned over the larynx of the subject and when the inflatable pad is in the inflated position.

The inflatable pad can be dimensioned to apply resistance to force of at least one of the digastric muscle, geniohyoid, and mylohyoid of the subject when the shell is positioned over the larynx of the subject and when the inflatable pad is in the inflated position.

The inflatable pad can be dimensioned to apply resistance to force of at least one infrahyoid muscle of the subject when the shell is positioned over the larynx of the subject and when the inflatable pad is in the inflated position.

The inflatable pad can be dimensioned to apply resistance to force of at least one muscle of a longitudinal muscle group of the subject when the shell is positioned over the larynx of the subject and when the inflatable pad is in the inflated position.

The inflatable pad can be dimensioned to apply resistance to force of at least one of the palatopharyngeus, stylopharyngeus and salpingopharyngeus of the subject when the shell is positioned over the larynx of the subject and when the inflatable pad is in the inflated position.

The inflatable pad can be dimensioned to apply resistance to force of at least one pharyngeal constrictor muscle of the subject when the shell is positioned over the larynx of the subject and when the inflatable pad is in the inflated position.

The inflatable pad can be dimensioned to increase resistance to a flow of swallowed food out of a pharynx of the subject when the shell is positioned over the larynx of the subject and when the inflatable pad is in the inflated position.

The inflatable pad can be dimensioned to apply resistance to superior and anterior movement of the larynx of the subject when the shell is positioned over the larynx of the subject and when the inflatable pad is in the inflated position.

The inflatable pad can be dimensioned to apply resistance to superior movement of a hyoid bone of the subject when the shell is positioned over the larynx of the subject and when the inflatable pad is in the inflated position.

The inflatable pad can be dimensioned to avoid applying pressure to a carotid artery of the subject when the shell is positioned over the larynx of the subject and when the inflatable pad is in the inflated position. The inflatable pad can be dimensioned to avoid applying pressure to a jugular vein of the subject when the shell is positioned over the larynx of the subject and when the inflatable pad is in the inflated position.

In one version of the device, a transverse cross-section of the proximal surface of the shell is concave. In another version of the device, a transverse cross-section of the proximal surface of the shell taken along a transverse axis of the shell is concave along an entire length of the transverse cross-section. In another version of the device, a longitudinal cross-section of the proximal surface of the shell is concave. In another version of the device, a longitudinal cross-section of the proximal surface of the shell taken along a longitudinal axis of the shell is concave along an entire length of the longitudinal cross-section. In another version of the device, a transverse cross-section of the proximal surface of the shell is concave, a longitudinal cross-section of the proximal surface of the shell is concave, and the longitudinal cross-section of the proximal surface is less concave than the transverse cross-section of the proximal surface.

In another version of the device, the shell is dimensioned to secure the shell around the neck of the subject such that the shell extends from cricoid cartilage to thyroid cartilage of the subject along a longitudinal axis of the shell. In another version of the device, the shell is dimensioned to secure the shell around the neck of the subject such that the shell extends from cricoid cartilage to above a hyoid bone of the subject along a longitudinal axis of the shell. In another version of the device, the proximal surface of the shell includes an indentation for receiving the inflatable pad.

In one version of the device, a viscoelastic layer is attached to a proximal side of the inflatable pad. The viscoelastic layer may comprise a shape memory foam. In another version of the device, a proximal layer covers a proximal side of the viscoelastic layer. The proximal layer can comprise a fabric.

In one version of the device, the device does not trigger swallowing in the subject. In another version of the device, the device does not include a vibrating element. In another version of the device, the device does not include an electrical element.

In one version of the device, the adjustable fastener includes a hook-type fastener component and a loop-type fastener component. In one version of the device, the device includes an inflation apparatus for inflating and deflating the inflatable pad, wherein the inflation apparatus includes a pump for inflating the inflatable pad, a conduit in fluid communication with the inflatable pad and the pump, and a valve for regulating inflation and deflation of the inflatable pad. The inflation apparatus may further comprise a gage for measuring a pressure level in the inflatable pad.

In another aspect, the present invention provides a method for improving swallowing function in a subject. The method comprises positioning a swallow exerciser device over the larynx of the subject. The swallow exerciser device includes (i) a shell having a longitudinal dimension such that the shell extends above a larynx of the subject and extends below the larynx of the subject wherein the shell has a distal surface and a proximal surface, (ii) an adjustable fastener that is dimensioned to secure the shell around a neck of the subject with the shell positioned over the larynx of the subject, and (iii) an inflatable conforming pad connected to the proximal surface of the shell wherein the inflatable pad is dimensioned to apply resistance to force of at least one swallowing muscle of the subject when the shell positioned over the larynx of the subject and when the inflatable pad is in an inflated position. In the method, the subject swallows after positioning the device over the larynx of the subject. When a subject repeatedly swallows with the swallow exerciser device positioned as in the method of the invention, the swallow exerciser device exercises the swallowing muscles and thereby strengthens the muscles involved in swallowing by making them "work harder".

In one version of the method, the adjustable fastener of the swallow exerciser device is connected to the shell. In another version of the method, a spacer (e.g., a bar) is positioned between the shell and the adjustable fastener of the swallow exerciser device, and the spacer is attached to the shell and/or the adjustable fastener. In another version of the method, the spacer of the swallow exerciser device is inwardly spaced from a perimeter edge of the shell.

In one version of the method, when the inflatable pad is in the inflated position, the inflatable pad exerts pressure between the shell and the neck of the subject in a pressure range of 10 to 50 mm Hg. In another version of the method, when the inflatable pad is in the inflated position, the inflatable pad exerts pressure between the shell and the neck of the subject in a pressure range of 10 to 40 mm Hg. In another version of the method, when the inflatable pad is in the inflated position, the inflatable pad exerts pressure between the shell and the neck of the subject in a pressure range of 10 to 30 mm Hg.

The method may further comprise increasing a pressure in the inflatable pad after the subject swallows at least one time. The method may further comprise removing the device after the subject swallows at least one time with a first pressure in the inflatable pad, and positioning the swallow exerciser device over the larynx of the subject a second time with a second pressure in the inflatable pad, wherein the second pressure is greater than the first pressure. The method may further comprise removing the device after the subject swallows at least one time with the second pressure in the inflatable pad, and positioning the swallow exerciser device over the larynx of the subject a third time with a third pressure in the inflatable pad, wherein the third pressure is greater than the second pressure.

In one version of the method, the device is positioned such that the shell extends about 1 to 2 centimeters above the larynx and the shell extends about 1 to 2 centimeters below the larynx. In another version of the method, the device is positioned such that the inflatable pad applies resistance to force of at least one muscle of the tongue of the subject when the inflatable pad is in the inflated position. In another version of the method, the device is positioned such that the inflatable pad applies resistance to force of at least one suprahyoid muscle of the subject when the inflatable pad is in the inflated position.

In another version of the method, the device is positioned such that the inflatable pad applies resistance to force of at least one infrahyoid muscle of the subject when the inflatable pad is in the inflated position.

In another version of the method, the device is positioned such that the inflatable pad applies resistance to force of at least one of the palatopharyngeus, stylopharyngeus and salpingopharyngeus of the subject when the inflatable pad is in the inflated position.

In another version of the method, the device is positioned such that the inflatable pad applies resistance to force of at least one pharyngeal constrictor muscle of the subject when the inflatable pad is in the inflated position.

In one version of the method, the method fatigues a pharynx of the subject. In another version of the method, the method fatigues a proximal striated esophagus of the subject. In another version of the method, the method fatigues both a pharynx and a proximal striated esophagus of the subject. In another version of the method, the method provides a resistive load to anterior and superior movement of a hyoid and a larynx of the subject.

It is therefore an advantage of the invention to provide a swallow exerciser device that can be used with the body's natural function (swallowing) to exercise the swallowing muscles.

It is another advantage of the invention to provide a swallow exerciser device that does not require the use of a vibrating element or an electrical element.

It is yet another advantage of the invention to provide a swallow exerciser device that does not trigger swallowing.

By working the swallowing muscles to fatigue with a swallow exerciser device of the invention, a user causes an increase in the strength of the swallowing muscles.

These and other features, aspects, and advantages of the present invention will become better understood upon consideration of the following detailed description, drawings and appended claims.

BRIEF DESCRIPTION OF THE DRAWINGS

FIG. 23 shows graphs of the effect of exerciser load of the swallow exerciser device of the invention on the pharyngeal contractile integral (PhCI) with and without use of the swallow exerciser device of the present disclosure.

Like reference numerals will be used to refer to like parts from Figure to Figure in the following description of the drawings.

DETAILED DESCRIPTION OF THE INVENTION

Figure 1:
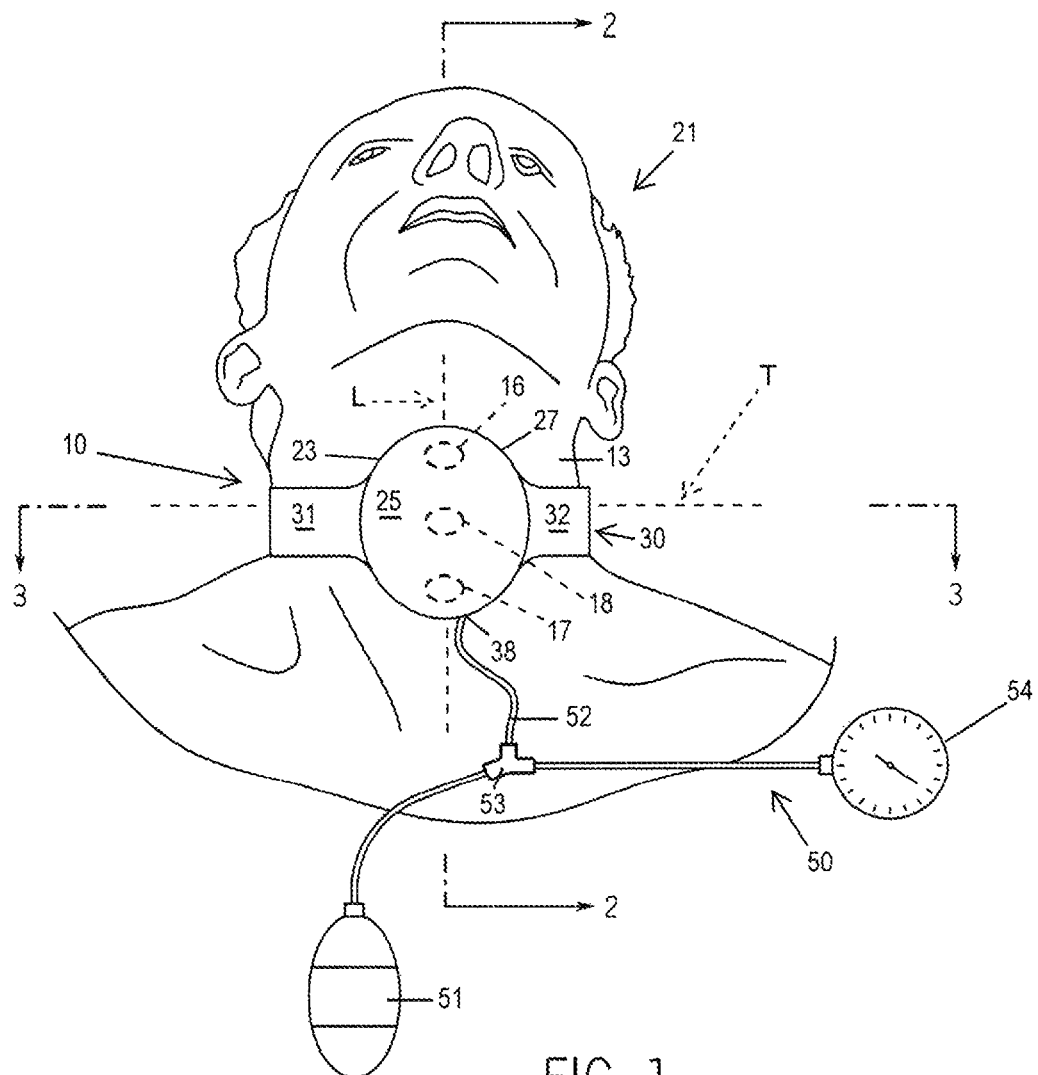
FIG. 1 is a front view of a subject wearing a swallow exerciser device according to one embodiment of the invention.
Figure 2:
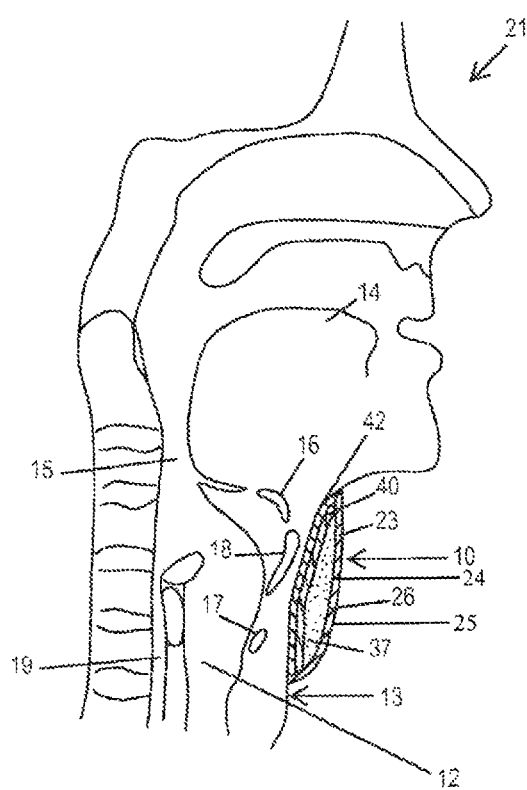
FIG. 2 is a longitudinal cross-sectional view of the swallow exerciser device of FIG. 1 taken along line 2-2 of FIG. 1.
Figure 3:
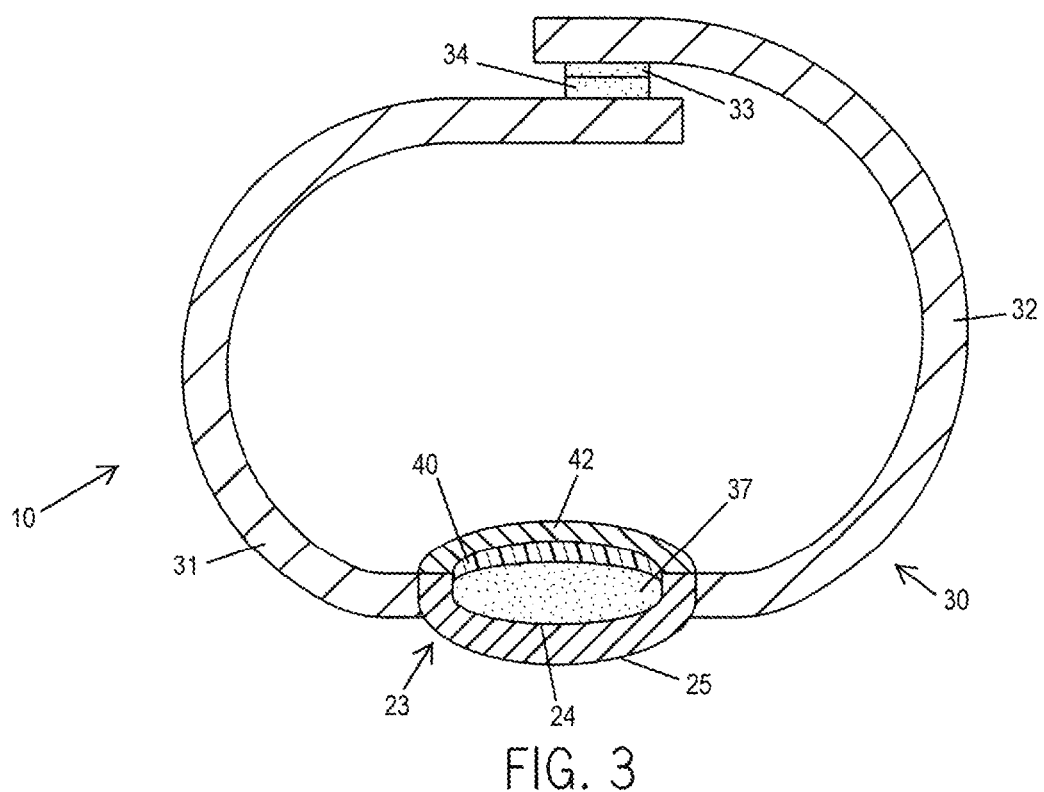
FIG. 3 is a transverse cross-sectional view of the swallow exerciser device of FIG. 1 taken along line 3-3 of FIG. 1.

Looking at FIGS. 1 to 3, there is shown a swallow exerciser device 10 according to one non-limiting embodiment of the invention positioned on the neck 13 of a human subject 21. The human subject 21 has anatomical features shown including a larynx 12, a neck 13, a tongue 14, a pharynx 15, hyoid bone 16, cricoid cartilage 17, thyroid cartilage 18 (Adam's apple), and an esophagus 19. The swallow exerciser device 10 shown has a shell 23, an adjustable fastener 30, and an inflation apparatus 50 for inflating and deflating an inflatable pad 37.

The shell 23 in the non-limiting embodiment shown has a generally oval perimeter edge 27. The shell 23 has a distal surface 24 and a proximal surface 25. The shell 23 may comprise a rigid polymeric material such as a polyolefin (e.g., polyethylene, polypropylene), a polyurethane, or a polycarbonate. The thickness of the shell 23 may be, for example, 1 to 5 millimeters.

In one embodiment, the shell 23 has an overall longitudinal dimension taken along its longitudinal axis L (see FIG. 1) such that the shell 23 extends above the larynx 12 of the subject 21 and extends below the larynx 12 of the subject 21. In another embodiment, the shell 23 has an overall longitudinal dimension taken along the longitudinal axis L such that the shell 23 extends from cricoid cartilage 17 to thyroid cartilage 18 of the subject 21. In another embodiment, the shell 23 has an overall longitudinal dimension taken along the longitudinal axis L such that the shell 23 extends from cricoid cartilage 17 to above a hyoid bone 16 of the subject 21. In another embodiment, the shell 23 has an overall longitudinal dimension taken along the longitudinal axis L of about 5 centimeters. In another embodiment, the shell 23 has an overall longitudinal dimension taken along the longitudinal axis L of about 4 centimeters. In another embodiment, the shell 23 has an overall longitudinal dimension taken along the longitudinal axis L of about 3 centimeters. In another embodiment, the shell 23 has a transverse dimension taken along the transverse axis T (see FIG. 1) of about 2 to about 5 centimeters.

Referring to FIG. 2, a longitudinal cross-sectional view of the swallow exerciser device 10 shows one non-limiting example positioning of the swallow exerciser device 10 with relation to several anatomical features. As can be seen, the longitudinally concave shell 23 extends from below the cricoid cartilage 17 to above the hyoid bone 16. When in use during a swallow, an external pressure applied to the subject's neck via the swallow exerciser device 10 provides resistance to the larynx 12 and hyoid 16 being drawn superiorly and anteriorly by swallowing muscles.

As shown in FIG. 2, a longitudinal cross-section of the proximal surface 25 of the shell 23 taken along the longitudinal axis L of the shell 23 is concave. In one embodiment, the longitudinal cross-section of the proximal surface 25 of the shell 23 taken along longitudinal axis L of the shell 23 is concave along an entire length of the longitudinal cross-section.

As shown in FIG. 3, a transverse cross-section of the proximal surface 25 of the shell 23 is concave. The transverse cross-section of the proximal surface 25 of the shell 23 taken along a transverse axis T (see FIG. 1) of the shell 23 is concave along an entire length of the transverse cross-section. In one embodiment, the longitudinal cross-section of the proximal surface 25 is less concave than the transverse cross-section of the proximal surface 25.

Referring to FIGS. 1 and 3, the adjustable fastener 30 of the exerciser device 10 comprises a first band 31 attached on one side of the perimeter edge 27 of the shell 23 and a second band 32 attached on an opposite side of the perimeter edge 27 of the shell 23. The first band 31 has a hook-type fastener component 34 at its distal end section, and the second band 32 has a loop-type fastener component 33 at its distal end section. The hook and loop fastener arrangement may be one sold under the trademark Velcro. The adjustable fastener 30 allows the shell to be secured around the neck 13 of the subject 21 as shown in FIGS. 1 and 2 via the hook and loop fastener arrangement.

The inflatable pad 37 is secured to the shell 23 in an indentation 26 in the distal surface 24 of the shell 23. The inflation apparatus 50 includes a pump 51, a conduit 52 which allows for fluid (e.g., air) flow between the pump 51 and the inflatable pad 37, and a valve 53 for regulating inflation and deflation of the pad 37. Additionally, a pressure gage 54 is used to measure a pressure level in the pad 37. The inflatable pad 37 is in fluid communication with a port 38 for releasably connecting the conduit 52 when inflating and deflating the inflatable pad 37. The port 38 may also include a valve for controlling the flow of air into the inflatable pad 37. The inflatable pad 37 can be inflated by squeezing the pump 51 which can be in the form of a bulb. The pressure produced by inflatable pad 37 can then be read using the gage 54. The gage 54 may be connected via a tube that is long enough for the subject to be able to read the gage 54. In other implementations, the bulb-type pump 51 may be replaced with means to automatically insert pressurized air into inflatable pad 37, such as an air pump.

In the non-limiting embodiment of the swallow exerciser device 10 in FIGS. 1-3, a viscoelastic layer 40 is attached to a proximal side of the inflatable pad 37. The viscoelastic layer may comprise a shape memory foam. The memory foam may be a viscoelastic open cell polyurethane foam which softens in reaction to body heat, allowing it to mold to a warm body in a few minutes. Some memory foam attributes include viscoelasticity which allows the foam to compress gradually, and memory, which means the foam returns to shape gradually. The thickness of the viscoelastic layer 40 may be, for example, 5 to 10 millimeters.

In the embodiment of the swallow exerciser device 10 in FIGS. 1-3, the proximal layer 42 covers a proximal side of the viscoelastic layer 40. In one non-limiting form, the proximal layer 42 comprises a fabric such as a washable, woven or knitted material. Example materials suitable for the fabric include synthetic fibers, natural fibers, and combinations thereof, further including cottons, poly/cottons, fleeces, wools, flannels, polyesters, nylons, etc. A preferred fabric is soft and comfortable.

The inflatable pad 37 is dimensioned to apply resistance to force of at least one swallowing muscle of the subject when the shell 23 positioned over the larynx of the subject and when the inflatable pad is in an inflated position. The inflatable pad 37 may apply resistance to force of at least one muscle of the tongue of the subject. The inflatable pad 37 may apply resistance to force of at least one suprahyoid muscle of the subject. The inflatable pad 37 may apply resistance to force of at least one of the digastric muscle, geniohyoid, and mylohyoid of the subject. The inflatable pad 37 may apply resistance to force of at least one infrahyoid muscle of the subject. The inflatable pad 37 may apply resistance to force of at least one suprahyoid muscle of the subject. The inflatable pad 37 may apply resistance to force of at least one muscle of a longitudinal muscle group (e.g., palatopharyngeus, stylopharyngeus and salpingopharyngeus) of the subject. The inflatable pad 37 may apply resistance to force of at least one pharyngeal constrictor muscle (superior pharyngeal constrictor muscle, middle pharyngeal constrictor muscle, inferior pharyngeal constrictor muscle) of the subject.

In the swallow exerciser device 10, the inflatable pad 37 can be dimensioned to increase resistance to a flow of swallowed food out of a pharynx of the subject when the shell 23 is positioned over the larynx of the subject and when the inflatable pad is in the inflated position. The inflatable pad 37 can be dimensioned to apply resistance to superior and anterior movement of the larynx of the subject when the shell is positioned over the larynx of the subject and when the inflatable pad is in the inflated position. The inflatable pad 37 can be dimensioned to apply resistance to superior movement of a hyoid bone of the subject when the shell is positioned over the larynx of the subject and when the inflatable pad is in the inflated position. The inflatable pad 37 can be dimensioned to avoid applying pressure to a carotid artery of the subject when the shell positioned over the larynx of the subject and when the inflatable pad is in the inflated position. The inflatable pad 37 can be dimensioned to avoid applying pressure to a jugular vein of the subject when the shell positioned over the larynx of the subject and when the inflatable pad is in the inflated position.

Thus, a swallow exerciser device has been developed that exercises and thereby strengthens the muscles involved in swallowing by making them "work harder". In one non-limiting example embodiment, the swallow exerciser device is 10-15 centimeters long and is placed around the neck covering the larynx extending 1-2 centimeters above and below the larynx. The swallow exerciser device includes rigid plastic shell with an indentation on the proximal ("patient") side which accommodates the inflatable pad. The pad can be inflated to apply graded amounts (e.g., 10-30 mm Hg) of pressure, as determined with a hand-held pressure gage. When the subjects swallow, this pressure induces graded degrees of resistance as the muscles of swallowing contract. These muscles can be of groups such as: (a) internal muscles of the oral cavity (e.g. pharynx, tongue, palate, etc.), and (b) external muscles (suprahyoid and thyrohyoid). The swallow exerciser device also induces resistance to the flow of swallowed material out of pharynx and into the esophagus.

Once the swallow exerciser device is fitted, the users participate in an exercise regimen. For example, 10 mm Hg is applied via the inflatable pad and the user swallows (or attempts to swallow, depending on his/her capabilities) thirty times at ten second intervals. This exercise set is repeated three times, three times per day for two weeks. The inflatable pad pressure is then increased to 20 mm Hg for the next two week cycle, and to 30 mm Hg for the following two week cycle and for future cycles. In another example, subjects will swallow repeatedly at a 30 second interval, morning, noon and in the evening for the lowest device pressure for a number of weeks (e.g., 2 weeks). Then the device pressure will be increased to the next level doing the same protocol for a number of weeks and so on.

Figure 4:
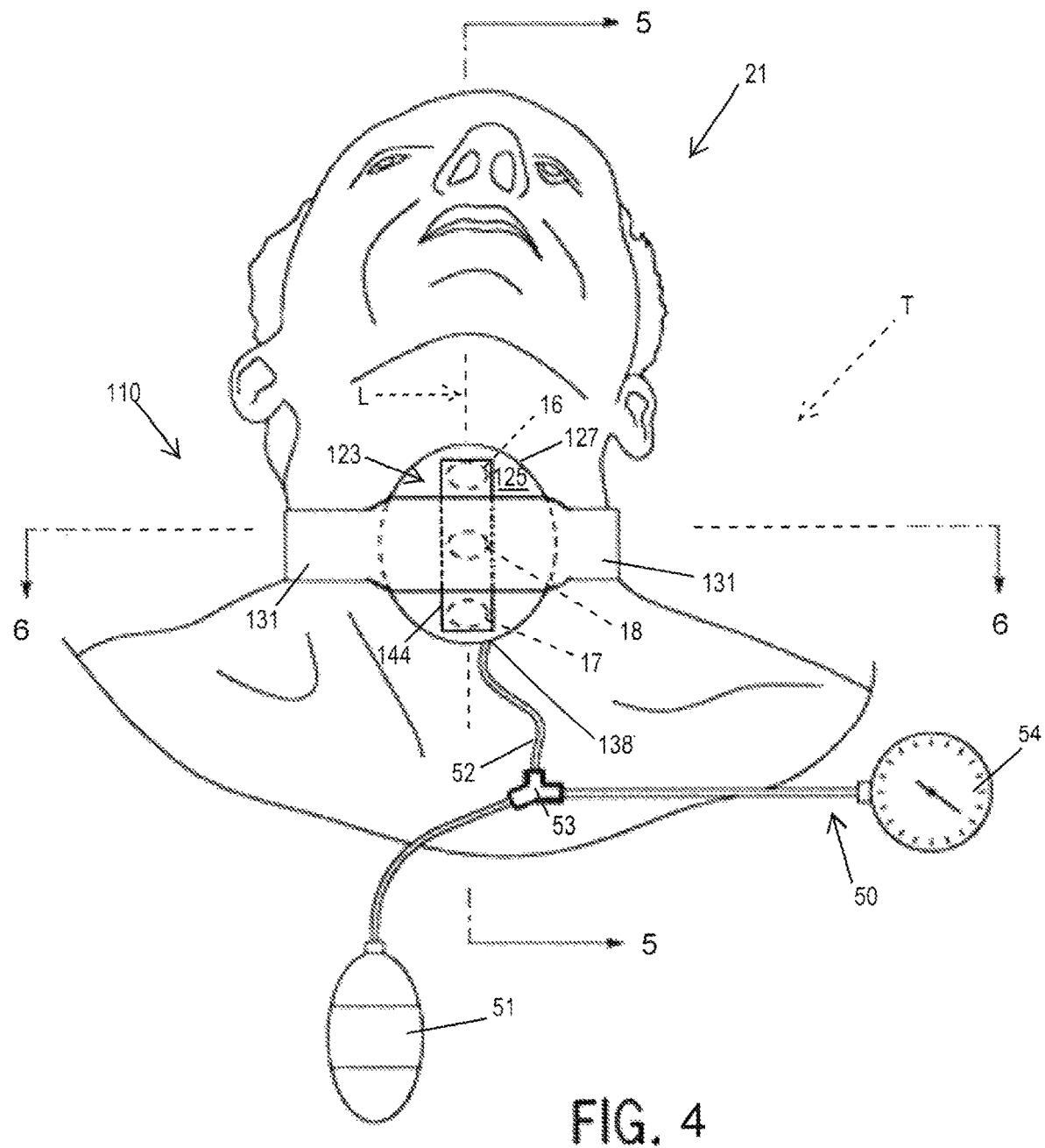
FIG. 4 is a front view of a subject wearing a swallow exerciser device according to another embodiment of the invention.
Figure 5:
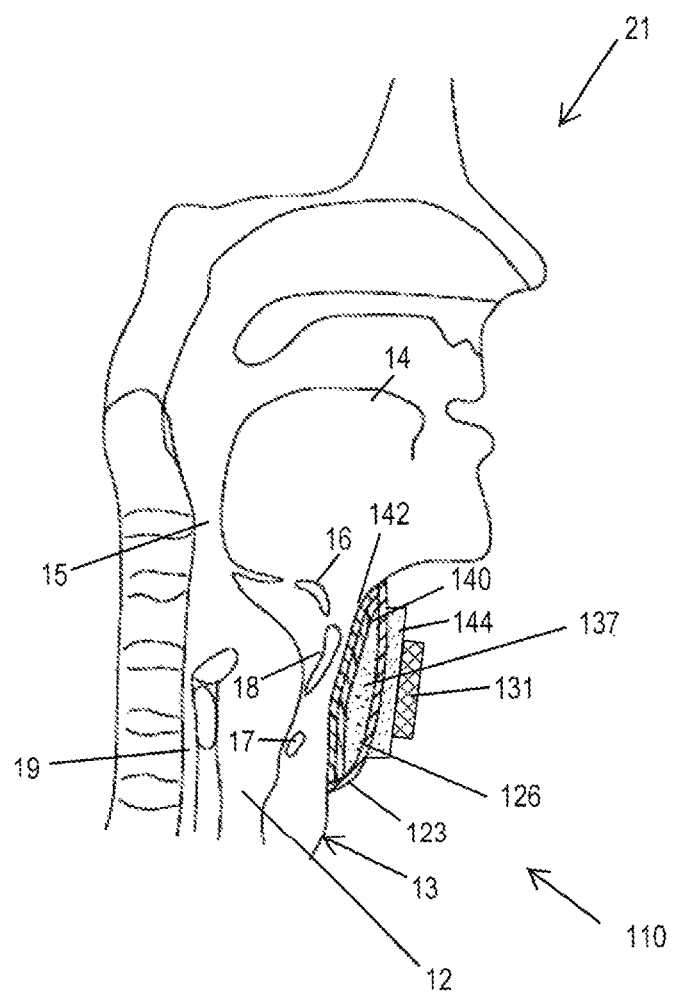
FIG. 5 is a longitudinal cross-sectional view of the swallow exerciser device of FIG. 4 taken along line 5-5 of FIG. 4.
Figure 6:
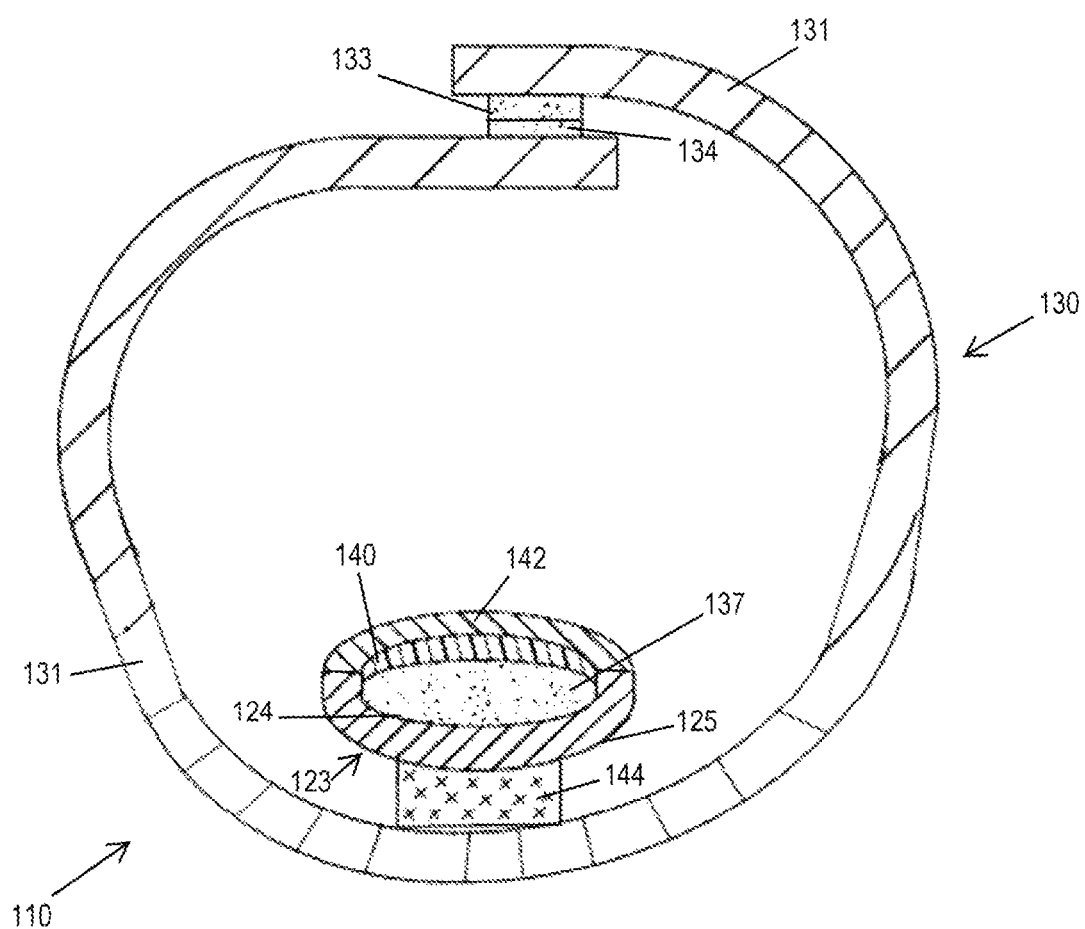
FIG. 6 is a transverse cross-sectional view of the swallow exerciser device of FIG. 4 taken along line 6-6 of FIG. 4.

Referring now to FIGS. 4-6, there is shown a swallow exerciser device 110 according to another non-limiting embodiment of the invention positioned on the neck 13 of a human subject 21. The human subject 21 has anatomical features shown including a larynx 12, a neck 13, a tongue 14, a pharynx 15, hyoid bone 16, cricoid cartilage 17, thyroid cartilage 18 (Adam's apple), and an esophagus 19. The swallow exerciser device 110 shown has a shell 123, an adjustable fastener 130, a spacer bar 144, and an inflation apparatus 50 for inflating and deflating an inflatable pad 137.

The shell 123 in the non-limiting embodiment shown has a generally oval perimeter edge 127. The shell 123 has a distal surface 124 and a proximal surface 125. The shell 123 may comprise a rigid polymeric material such as a polyolefin (e.g., polyethylene, polypropylene), a polyurethane, or a polycarbonate. The thickness of the shell 123 may be, for example, 1 to 5 millimeters.

In one embodiment, the shell 123 has an overall longitudinal dimension taken along its longitudinal axis L (see FIG. 4) such that the shell 123 extends above the larynx 12 of the subject 21 and extends below the larynx 12 of the subject 21. In another embodiment, the shell 123 has an overall longitudinal dimension taken along the longitudinal axis L such that the shell 123 extends from cricoid cartilage 17 to thyroid cartilage 18 of the subject 21. In another embodiment, the shell 123 has an overall longitudinal dimension taken along the longitudinal axis L such that the shell 123 extends from cricoid cartilage 17 to above a hyoid bone 16 of the subject 21. In another embodiment, the shell 123 has an overall longitudinal dimension taken along the longitudinal axis L of about 5 centimeters. In another embodiment, the shell 123 has an overall longitudinal dimension taken along the longitudinal axis L of about 4 centimeters. In another embodiment, the shell 123 has an overall longitudinal dimension taken along the longitudinal axis L of about 3 centimeters. In another embodiment, the shell 123 has a transverse dimension taken along the transverse axis T (see FIG. 4) of about 2 to about 5 centimeters.

Referring to FIG. 5, a longitudinal cross-sectional view of the swallow exerciser device 110 shows one non-limiting example positioning of the swallow exerciser device 110 with relation to several anatomical features. As can be seen, the longitudinally concave shell 123 extends from below the cricoid cartilage 17 to above the hyoid bone 16. When in use during a swallow, an external pressure applied to the subject's neck via the swallow exerciser device 110 provides resistance to the larynx 12 and hyoid 16 being drawn superiorly and anteriorly by swallowing muscles.

As shown in FIG. 5, a longitudinal cross-section of the proximal surface 125 of the shell 123 taken along the longitudinal axis L of the shell 123 is concave. In one embodiment, the longitudinal cross-section of the proximal surface 125 of the shell 123 taken along longitudinal axis L of the shell 123 is concave along an entire length of the longitudinal cross-section.

As shown in FIG. 6, a transverse cross-section of the proximal surface 125 of the shell 123 is concave. The transverse cross-section of the proximal surface 125 of the shell 123 taken along a transverse axis T (see FIG. 4) of the shell 123 is concave along an entire length of the transverse cross-section. In one embodiment, the longitudinal cross-section of the proximal surface 125 is less concave than the transverse cross-section of the proximal surface 125.

Referring to FIGS. 4 and 6, the adjustable fastener 130 of the exerciser device 110 comprises a band 131 that has a hook-type fastener component 134 at its distal end section and a loop-type fastener component 133 at its distal end section. The hook and loop fastener arrangement may be one sold under the trademark Velcro. The adjustable fastener 130 allows the shell to be secured around the neck 13 of the subject 21 as shown in FIGS. 4 and 5 via the hook and loop fastener arrangement.

The spacer bar 144 is attached to the shell 123 and/or the band 131, and is positioned between the shell 123 and the band 131 as shown in FIGS. 4-6. In one non-limiting example form, the spacer bar 144 has an overall longitudinal dimension taken along the longitudinal axis L (see FIG. 4) of about 3 to about 5 centimeters, a thickness of about 1 to about 2 centimeters, and a transverse dimension taken along the transverse axis T (see FIG. 4) of about 1 to about 2 centimeters. The spacer bar 144 is preferably spaced inward from the perimeter edge 127 of the shell 123. The spacer bar 144 serves to bridge the band 131 over the neck vital organs and prevent pressuring them. For example, the spacer bar 144 serves to bridge the band 131 over a carotid artery of the subject and a jugular vein of the subject when the shell is positioned over the larynx of the subject and when the inflatable pad is in the inflated position such that the carotid artery and the jugular vein of the subject are not pressured.

The inflatable pad 137 is secured to the shell 123 in an indentation 126 in the distal surface 124 of the shell 123. The inflation apparatus 50 includes a pump 51, a conduit 52 which allows for fluid (e.g., air) flow between the pump 51 and the inflatable pad 137, and a valve 53 for regulating inflation and deflation of the pad 137. Additionally, a pressure gage 54 is used to measure a pressure level in the pad 137. The inflatable pad 137 is in fluid communication with a port 138 for releasably connecting the conduit 52 when inflating and deflating the inflatable pad 137. The port 138 may also include a valve for controlling the flow of air into the inflatable pad 137. The inflatable pad 137 can be inflated by squeezing the pump 51 which can be in the form of a bulb. The pressure produced by inflatable pad 137 can then be read using the gage 54. The gage 54 may be connected via a tube that is long enough for the subject to be able to read the gage 54. In other implementations, the bulb-type pump 51 may be replaced with means to automatically insert pressurized air into inflatable pad 137, such as an air pump.

In the non-limiting embodiment of the swallow exerciser device 110 in FIGS. 4-6, a viscoelastic layer 140 is attached to a proximal side of the inflatable pad 137. The viscoelastic layer may comprise a shape memory foam. The memory foam may be a viscoelastic open cell polyurethane foam which softens in reaction to body heat, allowing it to mold to a warm body in a few minutes. Some memory foam attributes include viscoelasticity which allows the foam to compress gradually, and memory, which means the foam returns to shape gradually. The thickness of the viscoelastic layer 140 may be, for example, 5 to 10 millimeters.

In the embodiment of the swallow exerciser device 110 in FIGS. 4-6, the proximal layer 142 covers a proximal side of the viscoelastic layer 140. In one non-limiting form, the proximal layer 142 comprises a fabric such as a washable, woven or knitted material. Example materials suitable for the fabric include synthetic fibers, natural fibers, and combinations thereof, further including cottons, poly/cottons, fleeces, wools, flannels, polyesters, nylons, etc. A preferred fabric is soft and comfortable.

The inflatable pad 137 is dimensioned to apply resistance to force of at least one swallowing muscle of the subject when the shell 123 positioned over the larynx of the subject and when the inflatable pad is in an inflated position. The inflatable pad 137 may apply resistance to force of at least one muscle of the tongue of the subject. The inflatable pad 137 may apply resistance to force of at least one suprahyoid muscle of the subject. The inflatable pad 137 may apply resistance to force of at least one of the digastric muscle, geniohyoid, and mylohyoid of the subject. The inflatable pad 137 may apply resistance to force of at least one infrahyoid muscle of the subject. The inflatable pad 137 may apply resistance to force of at least one suprahyoid muscle of the subject. The inflatable pad 137 may apply resistance to force of at least one muscle of a longitudinal muscle group (e.g., palatopharyngeus, stylopharyngeus and salpingopharyngeus) of the subject. The inflatable pad 137 may apply resistance to force of at least one pharyngeal constrictor muscle (superior pharyngeal constrictor muscle, middle pharyngeal constrictor muscle, inferior pharyngeal constrictor muscle) of the subject.

In the swallow exerciser device 110, the inflatable pad 137 can be dimensioned to increase resistance to a flow of swallowed food out of a pharynx of the subject when the shell 123 is positioned over the larynx of the subject and when the inflatable pad is in the inflated position. The inflatable pad 137 can be dimensioned to apply resistance to superior and anterior movement of the larynx of the subject when the shell is positioned over the larynx of the subject and when the inflatable pad is in the inflated position. The inflatable pad 137 can be dimensioned to apply resistance to superior movement of a hyoid bone of the subject when the shell is positioned over the larynx of the subject and when the inflatable pad is in the inflated position. The inflatable pad 137 can be dimensioned to avoid applying pressure to a carotid artery of the subject when the shell positioned over the larynx of the subject and when the inflatable pad is in the inflated position.

Once the swallow exerciser device 110 is fitted, the users participate in an exercise regimen such as that described above for the swallow exerciser device 10.

EXAMPLES

The following Examples are provided in order to demonstrate and further illustrate certain embodiments and aspects of the present invention and are not to be construed as limiting the scope of the invention.

Data provided in the Examples demonstrates that exercise using the swallow exerciser device of the invention fatigues both the pharynx as well as the proximal striated esophagus thereby setting them up to be strengthened based on the proven and accepted notion in exercise physiology that exercises causing fatigue in the muscle result in strengthening of the muscle.

Example 1

Overview of Example 1

A swallow exerciser device of the present disclosure was shown to be effective for inducing fatigue in pharyngeal peristalsis. Fatigue is important because based on exercise physiology principles, muscles strengthen when they are fatigued by exercise.

Eleven healthy subjects (age 56±25 years, 6 female) were studied. The methods of this Example are based on fundamental deglutitive biomechanics wherein one of the prominent features of swallowing is anterior and superior movement of the hyoid and larynx. Compromised anterior and superior movement of the hyo-laryngeal complex has been shown in the elderly (see, Kern M, Bardan E, Arndorfer R, Hofmann C, Ren J, Shaker R., *Ann Otol Rhinol Laryngol.* 1999 October; 108(10):982-9; and Yokoyama M, Mitomi N, Tetsuka K, Tayama N, Niimi S., *Laryngoscope* 2000 March; 110(3 Pt 1):434-9; and Barikroo A, Carnaby G, Crary M., *Dysphagia* 2015 Jul. 11) as well as in patients with dysphagia of varying etiology (see, Paik N J, Kim S J, Lee H J, Jeon J Y, Lim J Y, Han T R., *J Electromyogr Kinesiol.* 2008 April; 18(2):329-35) including stroke (Kim Y, McCullough G H., *Dysphagia* 2010 March; 25(1):20-5) and cancer treatment. Dysphagia treatment using exercise has ranged from isotonic-isometric head raising (Shaker R, Kern M, Bardan E, Taylor A, Stewart E T, Hoffmann R G, Arndorfer R C, Hofmann C, Bonnevier J., *Am J Physiol.* 1997 June; 272(6 Pt 1):G1518-22; and Shaker R, Easterling C, Kern M, Nitschke T, Massey B, Daniels S, Grande B, Kazandjian M, Dikeman K., *Gastroenterology* 2002 May; 122(5):1314-21) to repeated effortful swallowing (Jang H J, Leigh J H, Seo H G, Han T R, Oh B M., *J Oral Rehabil.* 2015 May 25). These exercise regimens have been successful for improving swallowing performance in some patient groups, especially those patients wherein the primary cause of symptoms is associated with compromised upper esophageal sphincter (UES) opening. Given the prominent role of anterior and superior movement of the hyo-laryngeal complex during swallowing, the focus of the swallow exerciser device disclosed herein is to provide a resistive load to anterior and superior laryngeal movement thereby fatiguing muscle groups associated with deglutitive laryngeal movement. Effective and focused fatigue acts as a training mechanism for strengthening these muscle groups.

Resistance Exercise Device (RED)

In Example 1, we refer to a swallow exerciser device of the present disclosure as a Resistance Exercise Device (RED). To increase the load on the deglutitive muscles of the pharynx, a resistance exercise device (RED) was manufactured in our lab to provide an adjustable and fixed resistance to anterior and superior movement of the hyo-laryngeal complex. The device comprised a cotton fabric strap 63.5 centimeters in length and 2 centimeters in width. The ends of the strap were affixed with VELCRO® brand hook and loop fastening strips 21 centimeters in length to customize fitting of the RED when the strap is wrapped around the neck. For an initial device prototype, the middle portion of the device had an additional cotton pad 30 centimeters in length and 5 centimeters in width to provide support for the portion of the device that applies external force to the cricoid cartilage when positioned on the subject. A concave, flexible plastic disk was affixed to the middle of the strap assembly. This concave disk was wrapped in tape and serves as a support structure for an inflatable polyethylene bag which acts to apply an external force to the cricoid cartilage to restrict anterior and superior movement of the larynx. An inflatable bag was connected via a flexible catheter assembly to a hand pump and pressure gauge. During production of this device, the bag is maximally inflated on the bench and loosely wrapped with soft tape and subsequently deflated. In this way, the inflatable bag rests comfortably on the neck without skin irritation. The inflatable pad rests in a position on the cricoid fixed by closure of the VELCRO® brand hook and loop fastening straps. A known external force may be applied to the cricoid by partially inflating the bag to a specific pressure reading on the gauge. The soft and compliant bag conforms to the surface of the skin cradling the irregular geometry of the cricoid while applying a resistive force to anterior and superior distraction of the hyo-laryngeal complex during swallowing.

Pharyngeal and Proximal Esophageal Manometry

Pharyngeal and proximal esophageal pressure was monitored using a high resolution (HR) manometric catheter positioned transnasally to traverse the pharynx, upper esophageal sphincter (UES) and proximal esophagus. The HR probe and computerized recording and analysis system (ManoScan and ManoView Systems, Given Imaging, Inc., Duluth, Ga., USA) stores pressure data from 36 pressure sensors (with 1 centimeter sensor spacing) on the HR probe, displays the manometric information in topographic or line graph formats as well as provides post-acquisition analytic tools for parameterization of temporal and spatial pressure data.

Experimental Protocol

All subjects were seated in an upright position for the duration of the study. The subjects were verbally cued to perform 40 consecutive swallows of 0.5 ml room temperature water while wearing the RED during HR manometry. There was a 20 second interval between swallows wherein the subject refrained from swallowing. The water bolus was slowly injected into the oral cavity by a syringe and the subject was then cued to swallow the water in a single swallow. During these 40 swallows, the applied external pressure was maintained at 40 mmHg as measured by the external RED pressure gauge. Following these swallows, the RED was removed and, after a 20 minute rest period, another 40 swallows with 20 second intervals between swallows was recorded. During the 20 minute rest period, subjects remained seated with the manometric catheter in place and were told to relax and swallow ad libitum.

Manometric Parameters of Fatigue

Several manometric parameters were measured and analyzed for each swallow. Peak deglutitive peristaltic wave pressures were measured at positions 2, 3, 4, 5, 6, 7 and 8 centimeters above the upper margin of the manometrically determined pharyngo-esophageal high pressure zone. The deglutitive UES nadir pressure was also measured. Additionally, a parameter derived from the ManoView analysis software was measured. The pharyngeal contractile integral (PhCI) was calculated using the "SmartMouse" feature of the ManoView software. The contractile integral technique has been utilized in the distal esophagus as metric of "contractile vigor" (see, Lin Z, Roman S, Pandolfino J E, Kahrilas P J., *Neurogastroenterol Motil.* 2012 January; 24(1):e4-10) by multiplying the mean pressure amplitude times the contraction duration times the length of the region of interest. In the ManoView software topographic display using the computer's mouse, the contractile integral is calculated by scrolling out an area in the topographic display delineating a space-time box and logging the displayed contractile integral value. For the purposes of our analysis, the PhCI was characterized by circumscribing a space-time box in the topographic ManoView display to surround the pharyngeal deglutitive pressure recording with the upper margin of the box at the most proximal probe sensor at a time prior to deglutition and the distal margin of the box at the predetermined upper margin of the UES high pressure zone at the time of return of the high pressure zone to its resting manometric profile.

Both the peak peristaltic pressures and the PhCI were used as manometric surrogates for detecting fatigue due to repeated deglutitive pharyngeal contraction against the increased load provided by the RED. These metrics were also evaluated for the swallow sequences without the RED. In a second order analysis, the linear regression slope and correlation coefficient of the peak pressures and PhCI across sequential swallows was evaluated wherein a significant negative correlation (or a negative slope statistically different than zero) was associated with fatigue of the deglutitive pharyngeal muscles.

Statistical Analysis

Pearson correlation analysis was used to detect decreasing pharyngeal peak deglutitive peristaltic pressures and decreasing PhCI across consecutive water swallows. Slope values were compared for these parameters with and without the exerciser using the paired t-test.

Results

The pharyngeal contractile integrals showed slope differences between swallow tests with and without a swallow exerciser device of the present disclosure. Swallow against an increased external load induced by a swallow exerciser device of the present disclosure is effective for inducing fatigue in pharyngeal peristalsis.

Example 2

Overview of Example 2

Example 2 reports a study on the effect of a swallow exerciser device of the present disclosure on the proximal esophagus. Data in Example 2 clearly shows fatigue of the proximal esophageal muscles by swallowing while wearing the swallow exerciser device. Fatigue is important because based on exercise physiology principles, muscles strengthen when they are fatigued by exercise.

Among other things, the study of Example 2 sought to: (i) identify objective measurement parameters for proximal esophageal muscle; (ii) identify variability within measurement parameter methods, and (iii) observe any preliminary trends in the physiology and anatomy of proximal esophageal muscle response both with and without the swallow exerciser device.

Methods

A high resolution manometry (HRM) catheter was inserted through the nares of the patient and positioned so that it covered the entire pharynx (nasopharynx to proximal esophagus). The patient was situated upright, and was fitted with the swallow exerciser device, which was set to 40 mmHg for the study, around the larynx. The patient was given 20 minutes to adjust to catheter and swallow exerciser device. The patient was prompted to conduct 40 wet swallows of 0.5 ml of water with the swallow exerciser device on. The swallow was prompted every 20 seconds. The swallow exerciser device pressure was reset to 0 mmHg and the patient was given a 10 minute rest period. The patient was prompted to conduct 40 wet swallows of 0.5 ml of water without the swallow exerciser device on. The swallow was prompted every 20 seconds. Upon study conclusion, the catheter and swallow exerciser device were removed. All analysis was conducted blindly in Manoview ESO 3.0 software.

The demographics of the study were: 15 studies; 8 young (<40, 5 male/3 female); 6 elderly (>65, 1 male/5 female); 1 middle-age (41-64, male-male); all healthy; and 1 repeat (young).

Manometrically measured peristaltic pressure amplitude displays a well-defined trough called the "transition zone" (TZ). From manometry, the TZ center (nadir pressure amplitude) and the upper/lower margins of the pressure trough can quantified. Documented parameters of the study of Example 2 were: (1) contractile integral (CI, mmHg*cm*s) from bottom of UES to 3 centimeters, 4 centimeters, and 5 centimeters below the bottom of UES (striated esophagus); (2) Nadir pressure sensor location and pressure (TZ midpoint); and (3) CI from bottom of UES to nadir sensor location. Interpolated data was avoided for pressure measurements.

Figure 7:
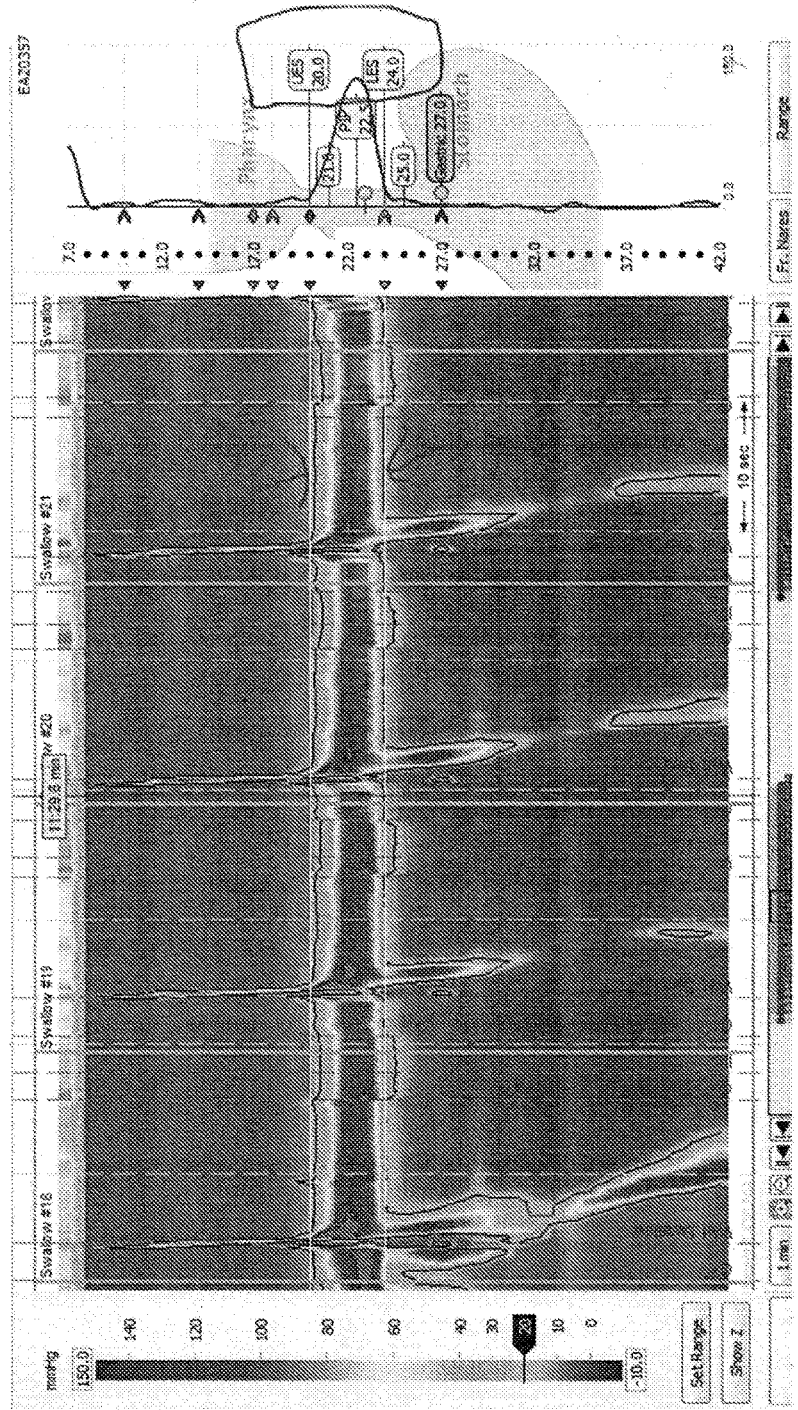
FIG. 7 is a contour plot from the recording device of a high resolution manometry (HRM) system. The HRM recording device produces a color-contour plot, with time on the x-axis, esophageal length on the y-axis, and pressure represented by a color scale. In the right side region of FIG. 7, the position of the pharynx, and the upper esophageal sphincter (UES) are depicted.

The margin was placed at the nearest centimeter outside of the resting UES 20 mmHg pressure zone. See FIG. 7.

Figure 8:
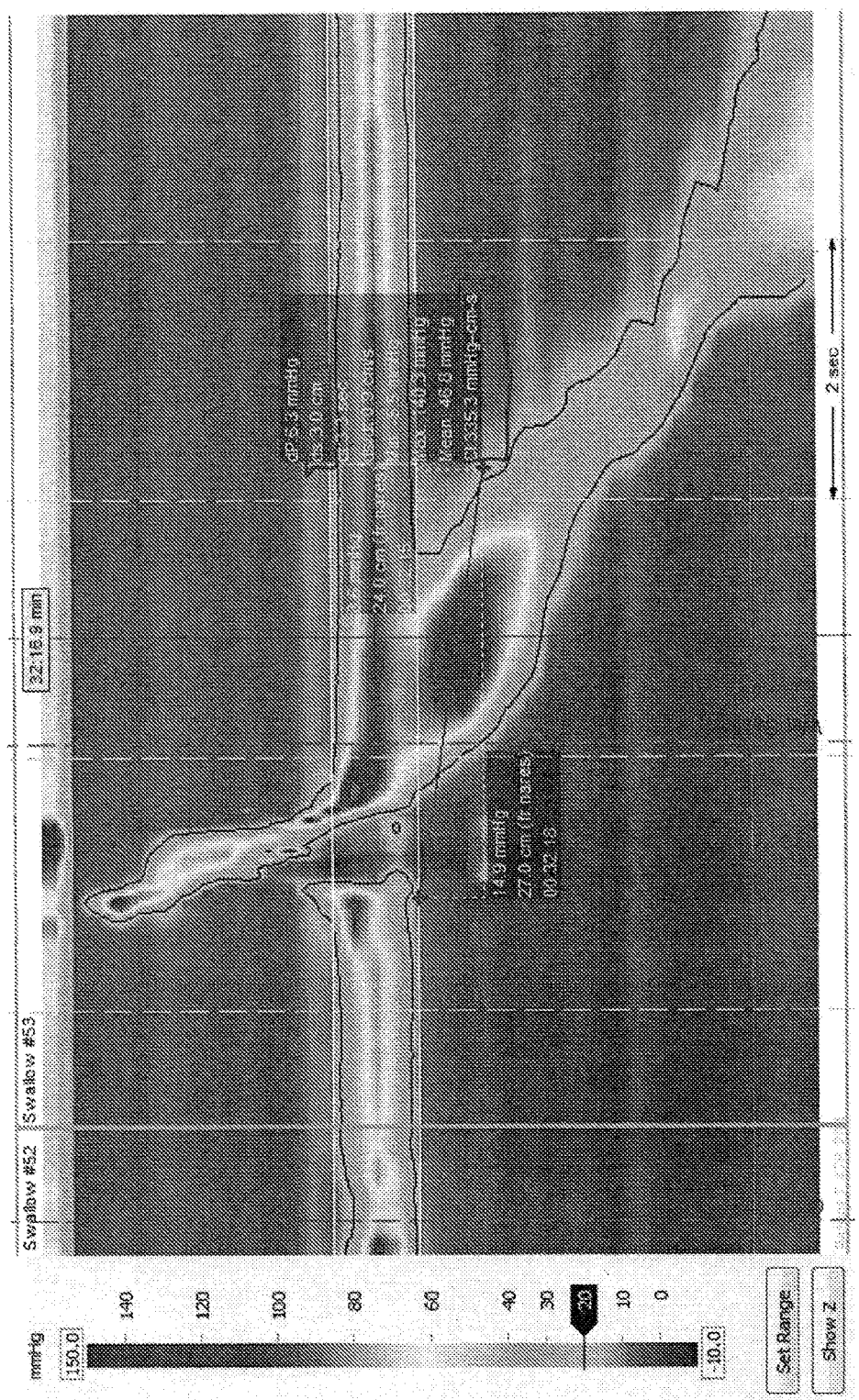
FIG. 8 is a contour plot from the recording device of a high resolution manometry (HRM) system showing how contractile integral (CI) can be measured using an HRM system.

FIG. 8 is a contour plot from the recording device of the HRM system showing how contractile integral (CI) was measured. Using a smart mouse, the CI at 20 mmHg was taken using: (a) the initiation of swallow as left margin; (b) the right most portion of striated swallow as right margin; (c) the lower margin of the UES as the top margin; and (d) the specified length as the bottom margin.

Figure 9:
FIG. 9 is a plot from the recording device of a high resolution manometry (HRM) system showing how nadir sensor can be identified using an HRM system.
Figure 10:
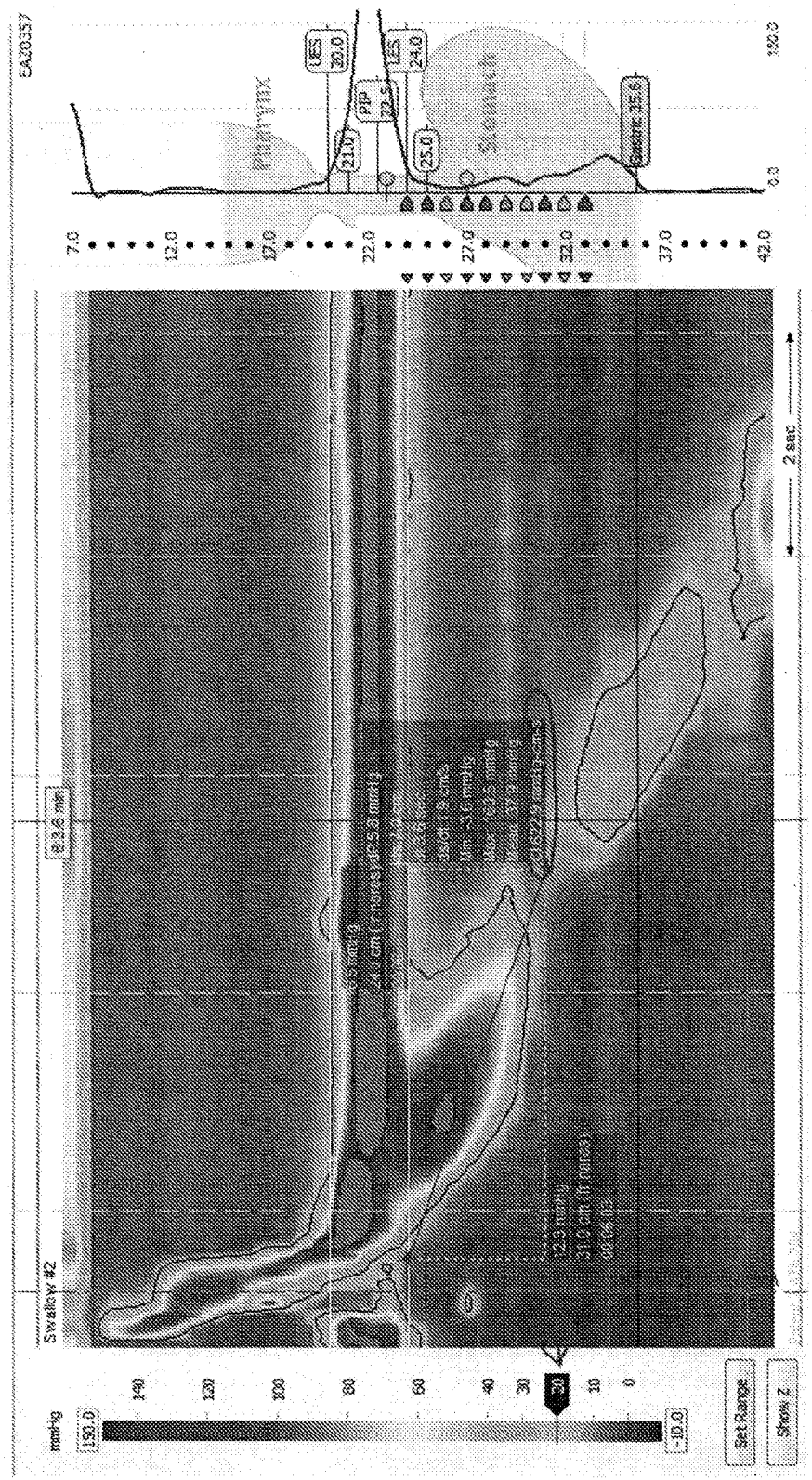
FIG. 10 is a plot from the recording device of a high resolution manometry (HRM) system showing how nadir sensor contractile integral (CI) can be identified using an HRM system.

FIG. 9 is a plot from the recording device of the HRM system showing how nadir sensor was identified, and FIG. 10 is a plot from the recording device of the HRM system showing how nadir sensor contractile integral (CI) was identified. We established 10 channels, 1 centimeter spaced, starting from the UES lower margin of the HPZ. They were placed at the X.0 cm mark. On the channel display, we identified the channel with the smallest peak pressure during the swallow. We repeated the contractile integral (CI) method, this time with the nadir sensor serving as the lower margin of the contractile integral (CI) box. Any peak pressure below 0 mmHg was documented as 0 mmHg.

Figure 11:
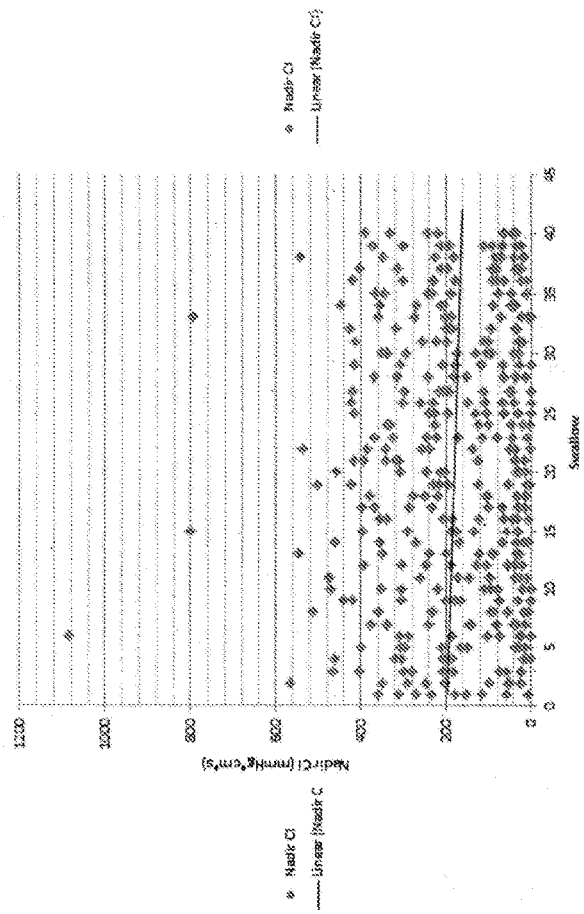
FIG. 11 shows an analysis of contractile integral (CI) slope.
Figure 11:
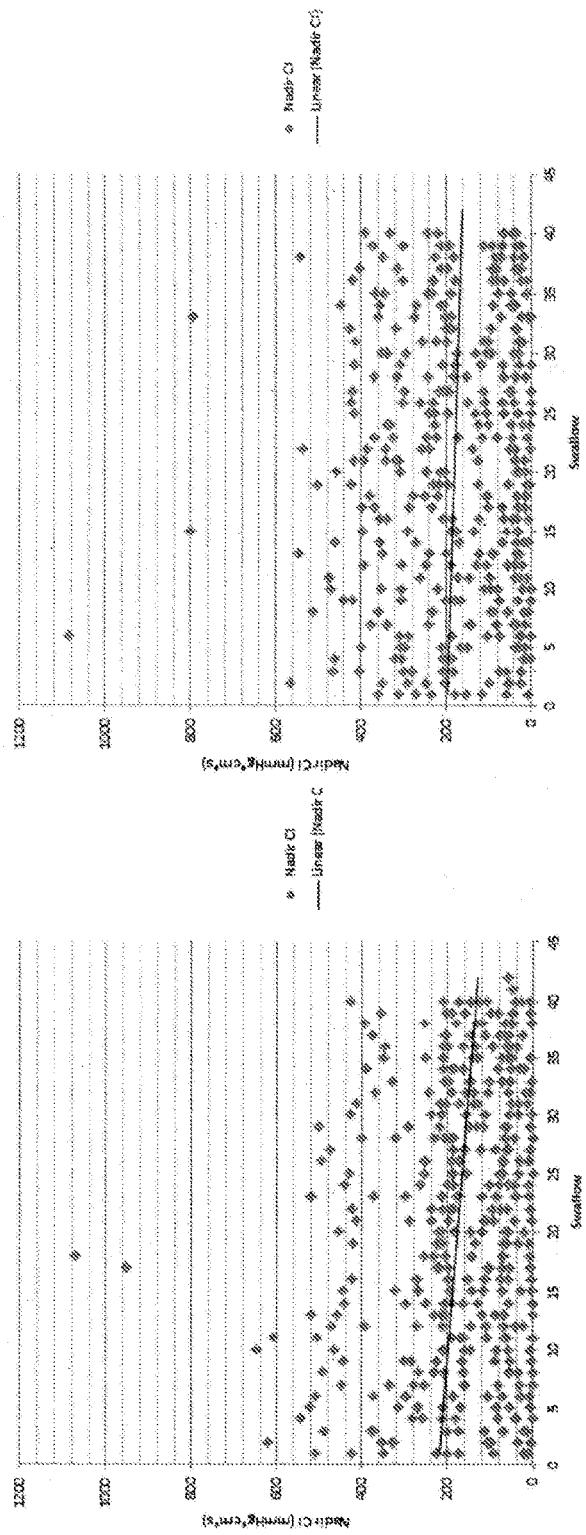
Figure 12:
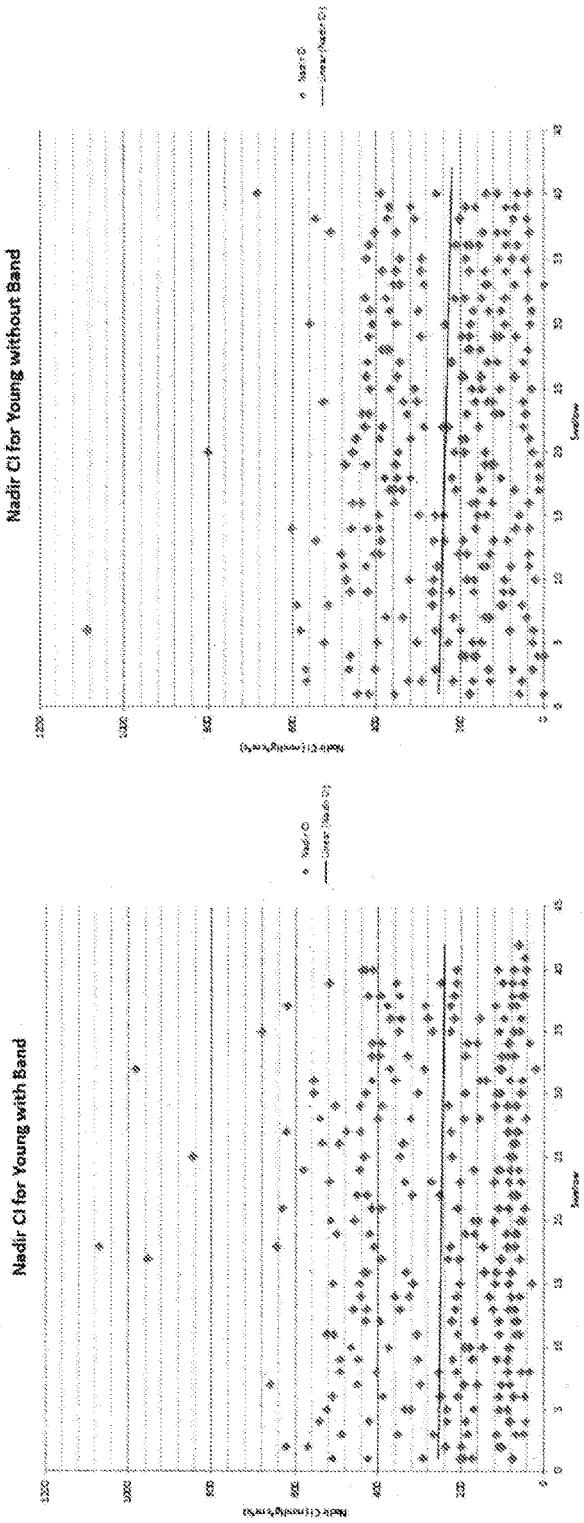
FIG. 12 shows another analysis of contractile integral (CI) slope by age.
Figure 13:
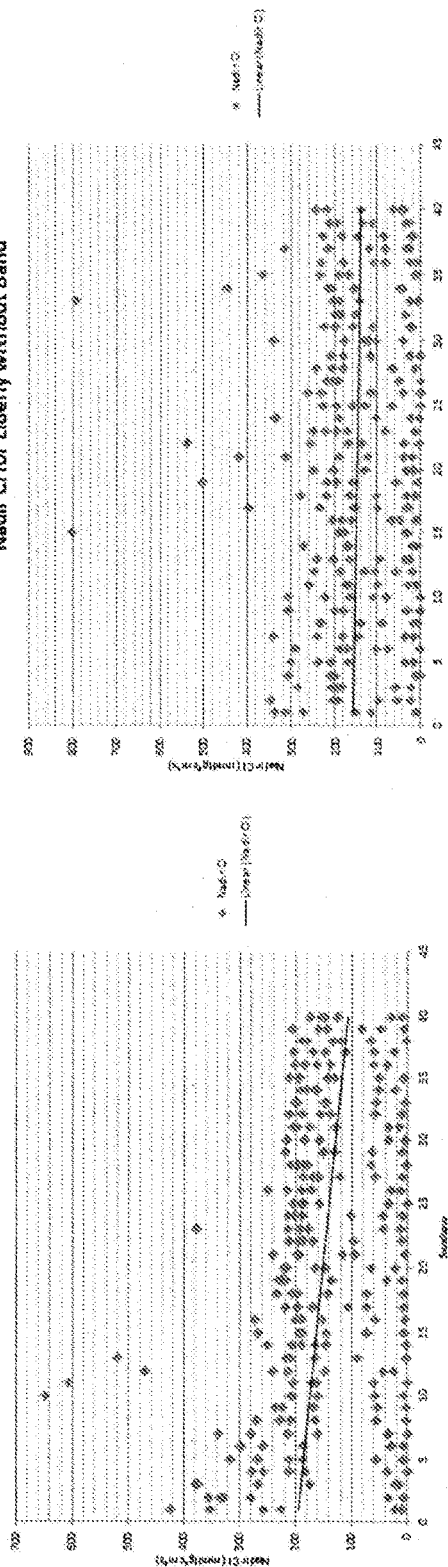
FIG. 13 shows another analysis of contractile integral (CI) slope by age.

FIG. 11 shows an analysis of contractile integral (CI) slope. We measured CI from the lower UES margin of the HPZ to 3 centimeters, 4 centimeters, and 5 centimeters below the lower UES margin of the HPZ, and to the nadir sensor and CI was plotted per swallow with and without the swallow exerciser device (rate of fatigue). The CI slope was compared and the data (n=9) is shown in FIG. 11 where Sig. Correlat.=Significant Correlation. The contractile integral (CI) slope by age was compared and the data (young n=7) is shown in FIG. 12. The CI slope by age was compared and the data (elderly n=6) is shown in FIG. 13.

Figure 14:
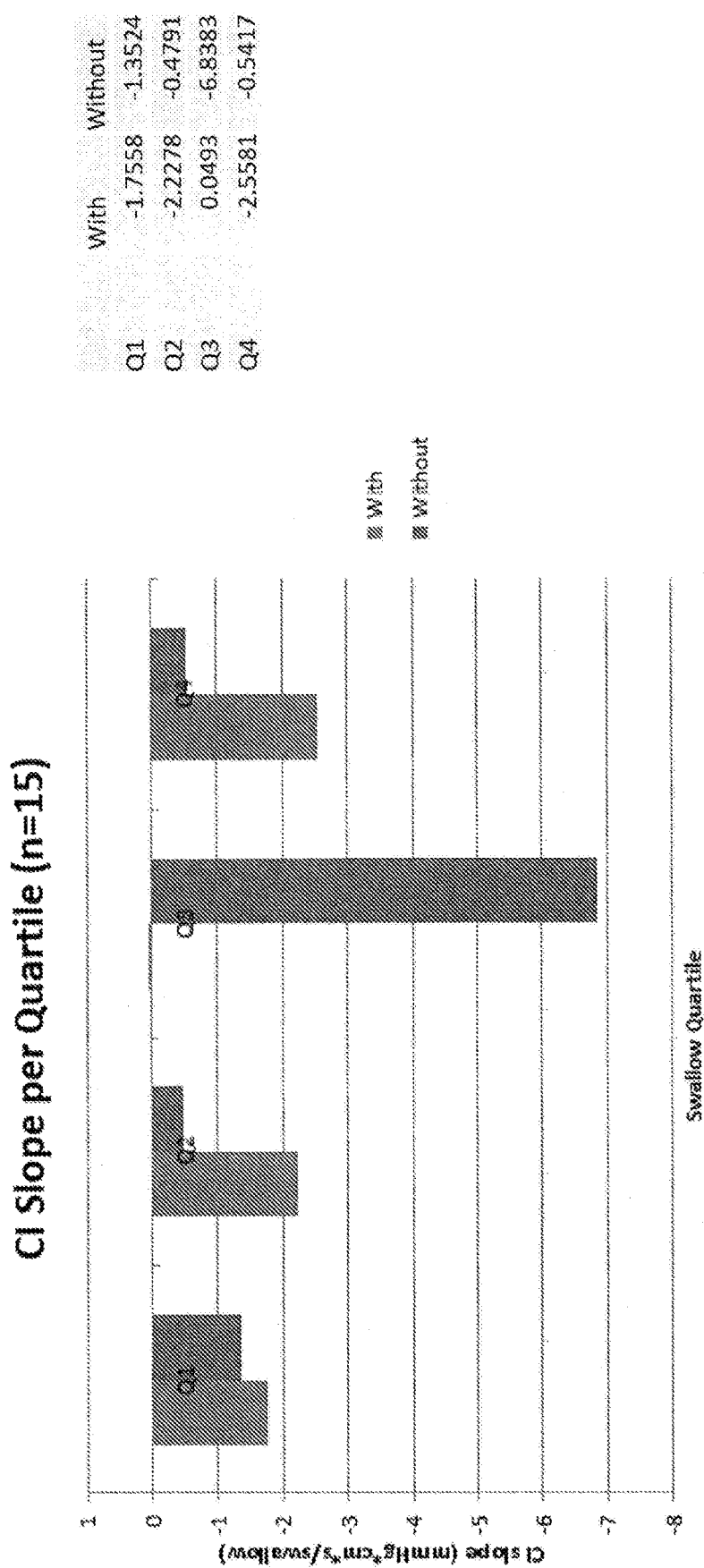
FIG. 14 shows an analysis of contractile integral (CI) slope per swallow quartile. The bars reading left to right in each group of the graph are in the same order as the right hand legend reading top to bottom.
Figure 15:
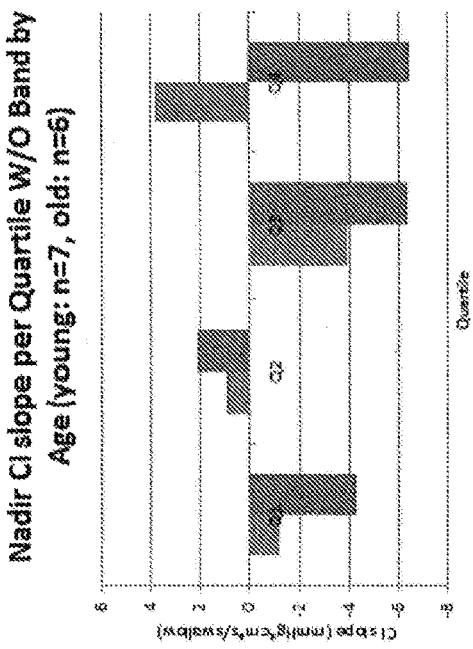
FIG. 15 shows another analysis of contractile integral (CI) slope per swallow quartile. The bars reading left to right in each group of the graph are in the same order as the right hand legend reading top to bottom.
Figure 15:
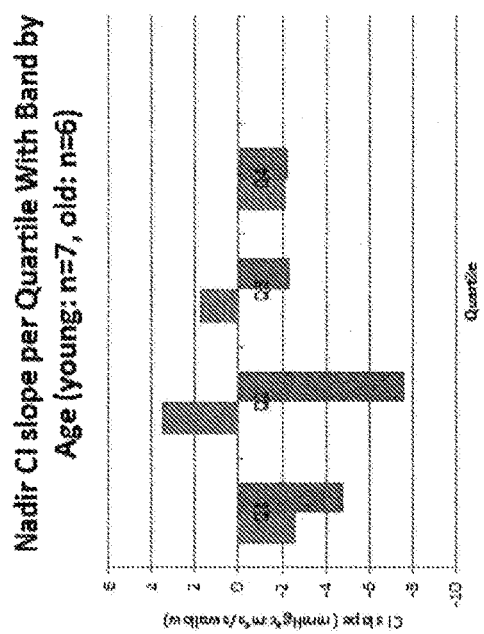
Figure 16:
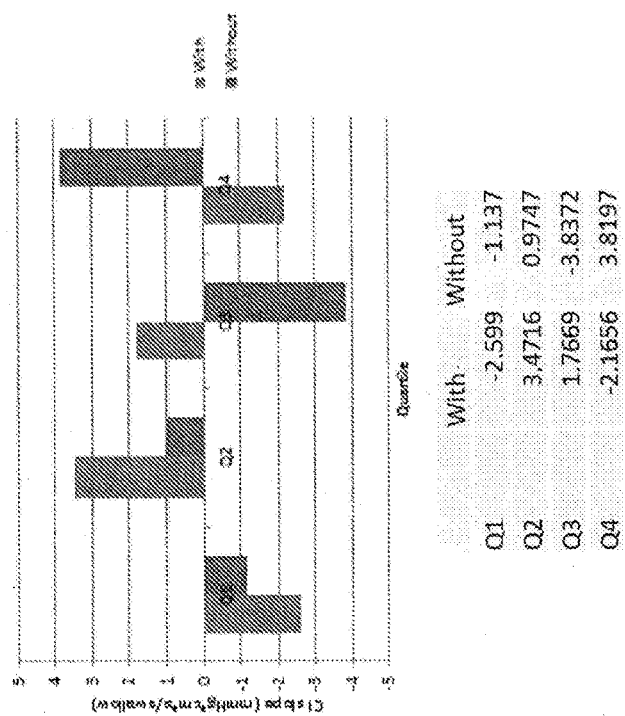
FIG. 16 shows another analysis of contractile integral (CI) slope per swallow quartile. The bars reading left to right in each group of the graph are in the same order as the right hand legend reading top to bottom.
Figure 16:
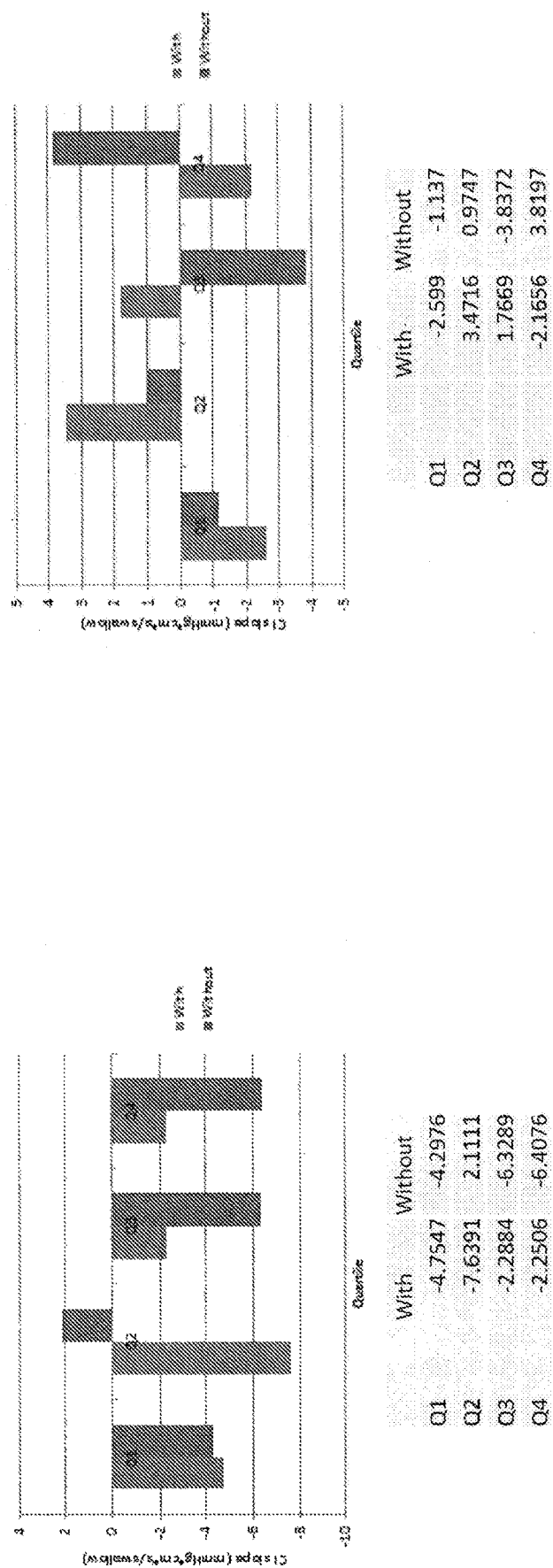
Figure 17:
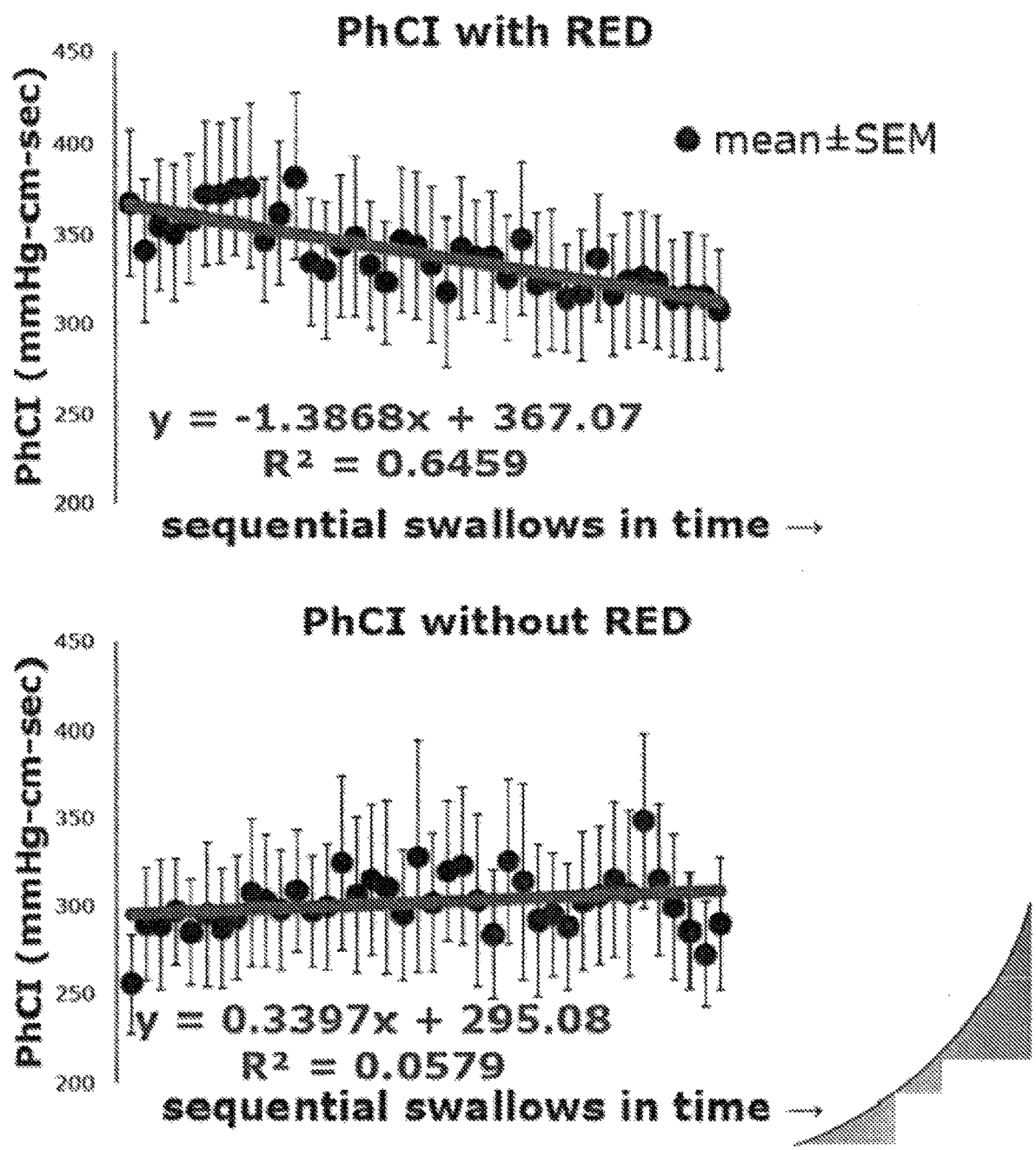
FIG. 17 shows graphs of the pharyngeal contractile integral (PhCI) with and without use of a swallow exerciser device of the present invention (referred to as a Resistance Exercise Device (RED) in FIG. 17).
Figure 18:
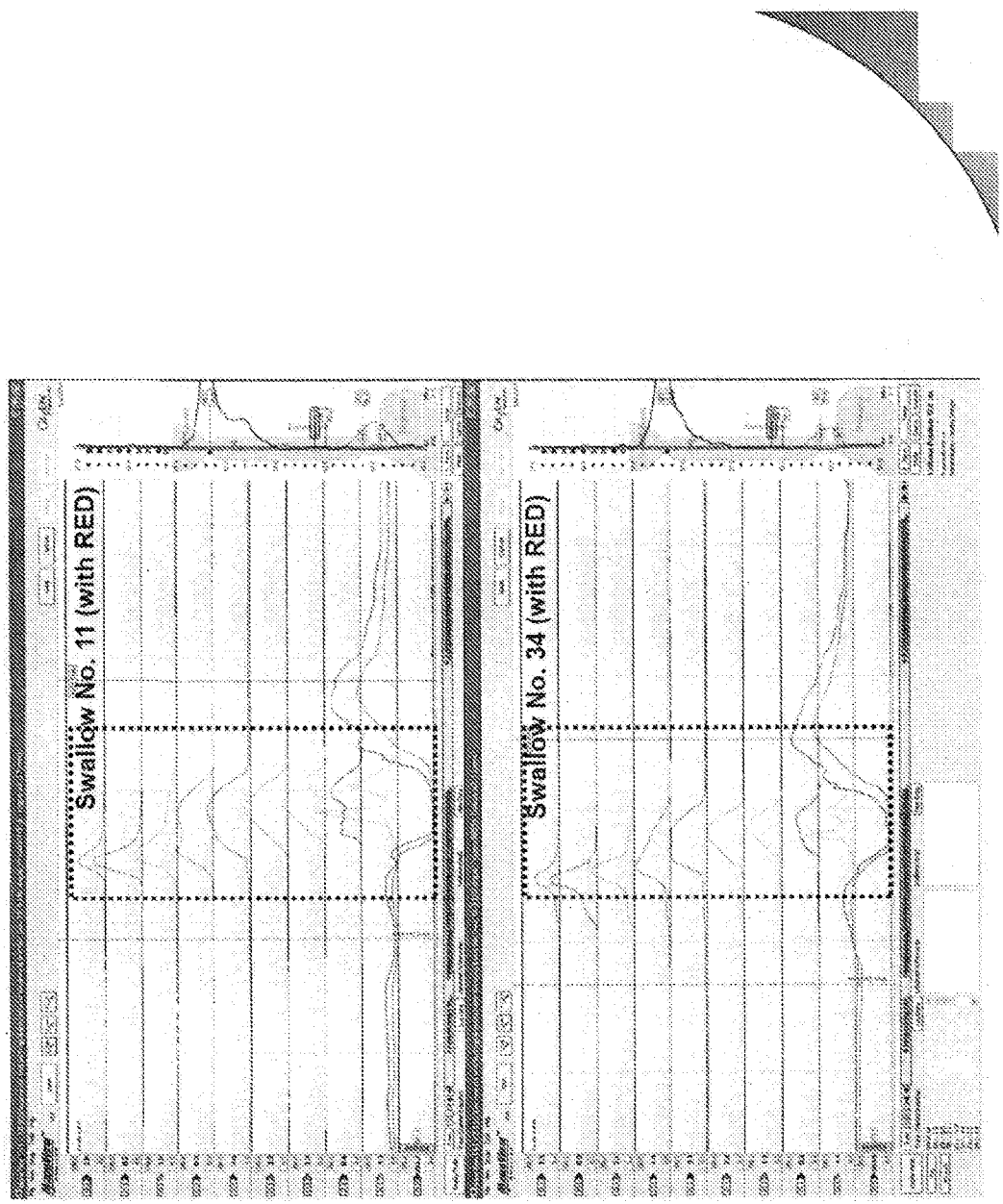
FIG. 18 shows graphs of the effect of the swallow exerciser device of the invention (referred to as a Resistance Exercise Device (RED) in FIG. 18) on pharyngeal peristalsis in sequential swallows.
Figure 19:
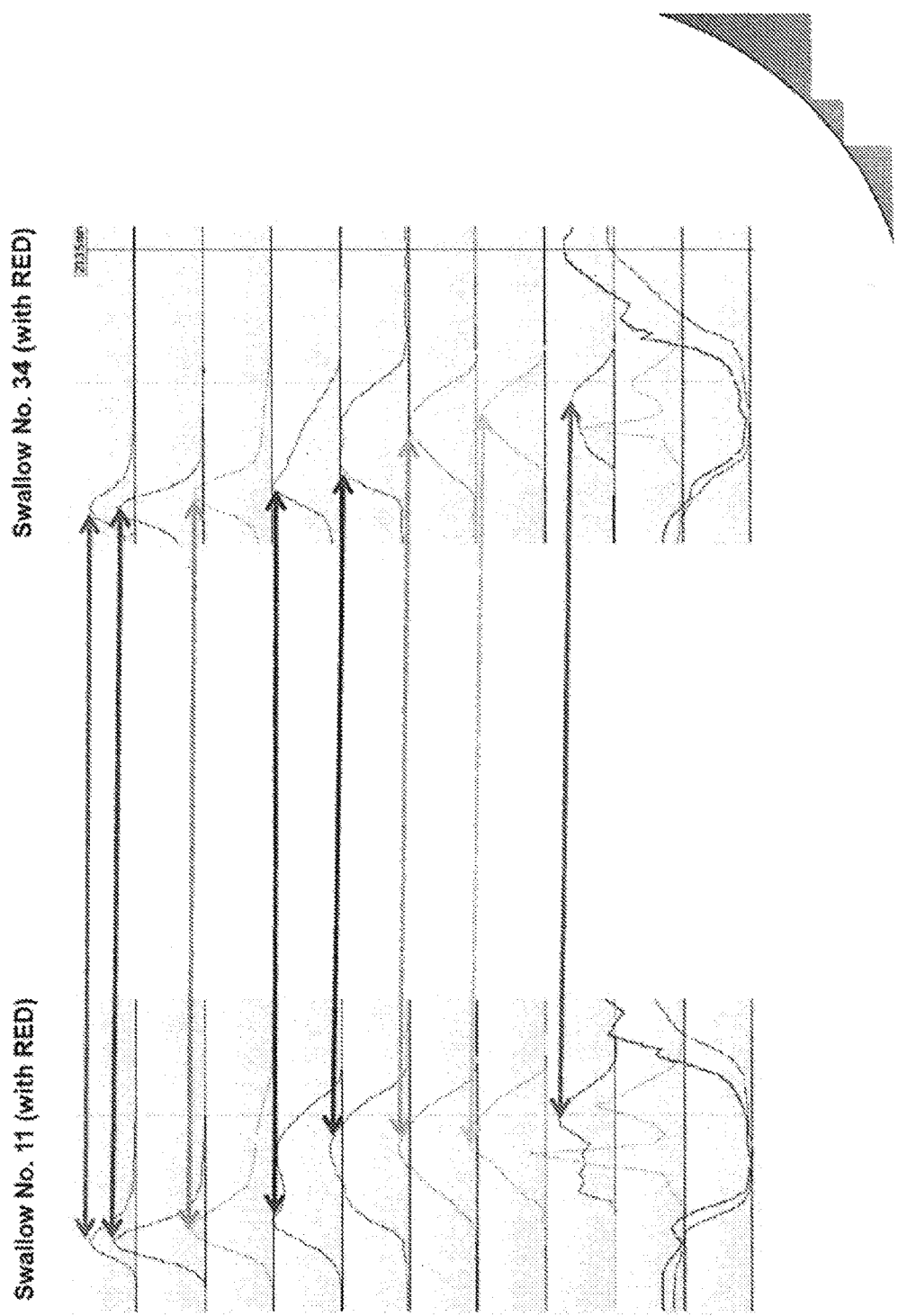
FIG. 19 shows graphs of the effect of the swallow exerciser device of the invention (referred to as a Resistance Exercise Device (RED) in FIG. 19) on pharyngeal peristalsis in sequential swallows. As seen by swallow number 34 in FIG. 19, the pharyngeal peristaltic pressures have decreased compared to earlier swallows indicating the fatigue of the pharyngeal muscles which is necessary for the muscles to strengthen by exercise.

FIGS. 14 to 16 show our analyses of contractile integral (CI) slope per swallow quartile. Each set of 40 swallows (both with and without the swallow exerciser device) was separated into 4 quartiles of 10 swallows each. The measured CI from the lower UES margin to 3 centimeters, 4 centimeters, and 5 centimeters below the lower UES margin, and to the nadir sensor, and CI was plotted per swallow for the designated quartile.

2-Person Inter-Observer Analysis: Out of the original 10, only 1 study had a different UES margin. CI average Correlation: 0.9568. Sensor selection average Correlation:

0.9855. Sensor Peak Pressure average Correlation: 0.8524. N=9 average correlation: 0.9039. N=10 w/different UES margin: 0.8921. N=10 w/edited UES margin: 0.8987

Conclusions

As noted above, the pharyngeal contractile integral (PhCI) can be used as a manometric surrogate for detecting fatigue due to the increased load provided by the swallow exerciser device of the present disclosure. In Example 2, the contractile integral (CI) shows statistically significant slope differences with a swallow exerciser device of the present disclosure, particularly in elderly subjects, suggesting fatigue. A potential pattern was exhibited in the CI quartile. Initial review of the parameters reveals relatively low inter-observer variability. Thus, swallow against an increased external load induced by a swallow exerciser device of the present disclosure is effective for inducing fatigue in the proximal esophagus.

Example 3

Overview of Example 3

Example 3 reports a study on the effect of a swallow exerciser device of the present disclosure for swallowing on pharyngeal peristalsis. Data in Example 3 clearly shows fatigue of the pharyngeal muscles by swallowing while wearing the swallow exerciser device. The pharyngeal muscles can be strengthened when they are fatigued by exercise.

Introduction

The oral/pharyngeal phase of swallowing involves complex interactions between lingual, pharyngeal, oral, cervical and laryngeal muscles. In addition to precise coordination, adequate contractile function of these muscles are crucial for normal transport of the swallowed bolus out of the pharynx and into the esophagus. The elements involved in a normal oral/pharyngeal phase of swallowing include: (i) motor function (tongue and pharynx); (ii) relaxation/opening (UES, suprahyoid muscles); (iii) airway closure (larynx, velopharynx); (iv) sensory function; and (v) coordination and timing. Weakness of the oropharyngeal musculature including the pharyngeal constrictors commonly occurs following stroke, radiation and surgical therapy. Weakness of pharyngeal peristalsis can result in dysphagia, post deglutitive residue, aspiration, and aspiration pneumonia. Various exercises have been shown to strengthen components of the oropharyngeal deglutitive apparatus such as the supra-hyoid UES opening muscles and the tongue. Options directly aimed at improving the contractile function of the pharynx however, are currently limited.

We hypothesized that repetitive swallowing against an increased load induced externally will result in fatigue of the pharyngeal muscles as evidenced by decrease in the peak amplitude of pharyngeal peristaltic pressure waves and that exercise induced muscle fatigue could yield strengthening that could improve pharyngeal function.

Among other things, the study of Example 3 sought to determine the effect of increased swallow load induced by applying resistance to the anterior and superior excursions of the hyo-laryngeal complex on the parameters of the pharyngeal peristaltic pressure waves.

Methods

We studied 15 healthy individuals of age 56±25 years (7 female) in an upright position. Pharyngeal peristalsis was recorded using an HRM catheter that covered the entire length of the pharynx, UES, and proximal esophagus. A reduction in the amplitude of pharyngeal peristalsis was considered as a surrogate for fatigue.

To increase the swallow load externally, we used a swallow exerciser device of the present disclosure that due to its configuration can induce graded resistance to the anterior and superior excursion of the hyo-laryngeal complex during swallowing. In Example 3 and its associated FIGS. 17-23, we refer to a swallow exerciser device of the present disclosure as a Resistance Exercise Device (RED).

We recorded pharyngeal peristalsis during 40 consecutive swallows of 0.5 ml water in 20 second intervals while subjects wearing the RED set at 40 mmHg pressure. This was followed after 15 minutes of rest by 40 swallows of the same volume and interval without the RED.

Parameters of interest included: (i) peak pharyngeal peristaltic pressures at 3, 4, 5, 6, 7 and 8 centimeters above the upper margin of pharyngo-esophageal high pressure zone (PE-HPZ), and (ii) pharyngeal contractile integral (PhCI). For statistical analyses, we used Pearson correlation, intra-class correlation and Student's t-test.

Results

We analyzed the effect of the Resistance Exercise Device (RED) on the pharyngeal contractile integral (PhCI). There is a progressive decrease in PhCI for sequential swallows while wearing the RED. See FIG. 17.

We analyzed the effect of the Resistance Exercise Device (RED) on pharyngeal contraction. The peak pressure of sequential swallows can be compared, see FIGS. 18-19. As seen by swallow number 34 in FIG. 19, the pharyngeal peristaltic pressures have decreased compared to earlier swallows indicating the fatigue of the pharyngeal muscles which is necessary for the muscles to strengthen by exercise.

Figure 20:
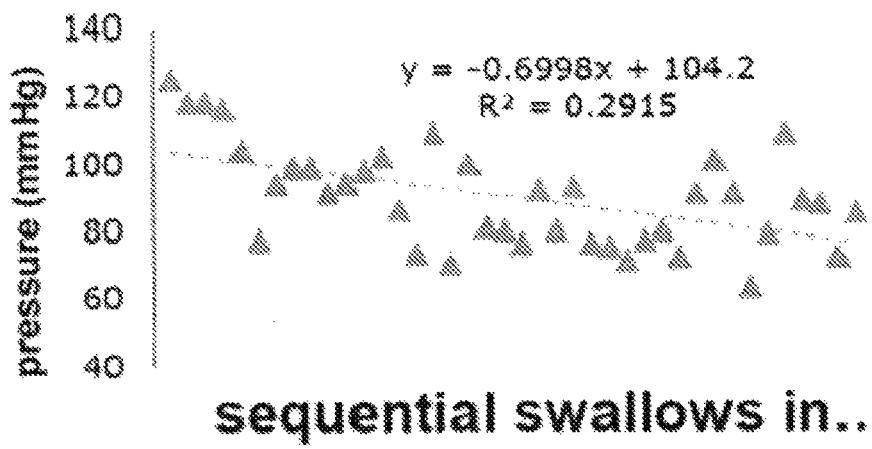
FIG. 20 shows graphs of the effect with and without use of a swallow exerciser device of the invention (referred to as a Resistance Exercise Device (RED) in FIG. 20) on pharyngeal contraction in the proximal pharynx.
Figure 20:
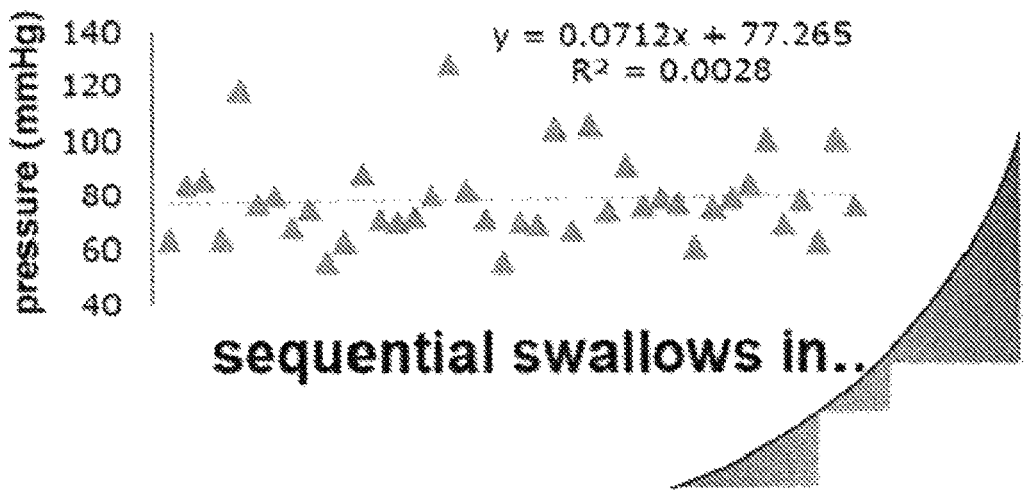

Referring to FIG. 20, there is shown peak deglutitive peristaltic wave amplitudes 8 centimeters above the upper margin of the PE-HPZ. There is a progressive decrease in peak pressure at this location for sequential swallows while wearing the RED. This decrease is absent for successive swallows without the RED.

Figure 21:
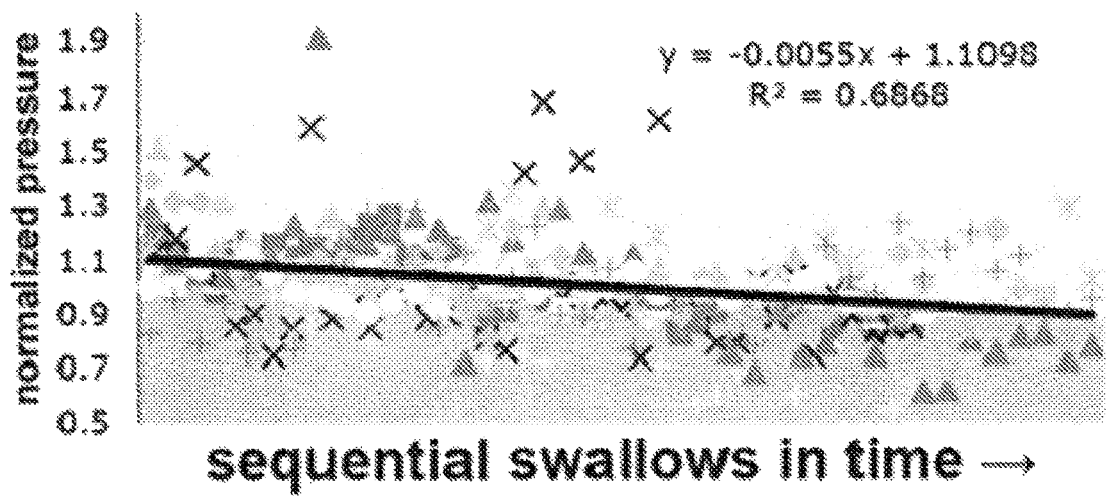
FIG. 21 shows graphs of the effect with and without use of a swallow exerciser device of the invention (referred to as a Resistance Exercise Device (RED) in FIG. 21) on pharyngeal contraction.
Figure 21:
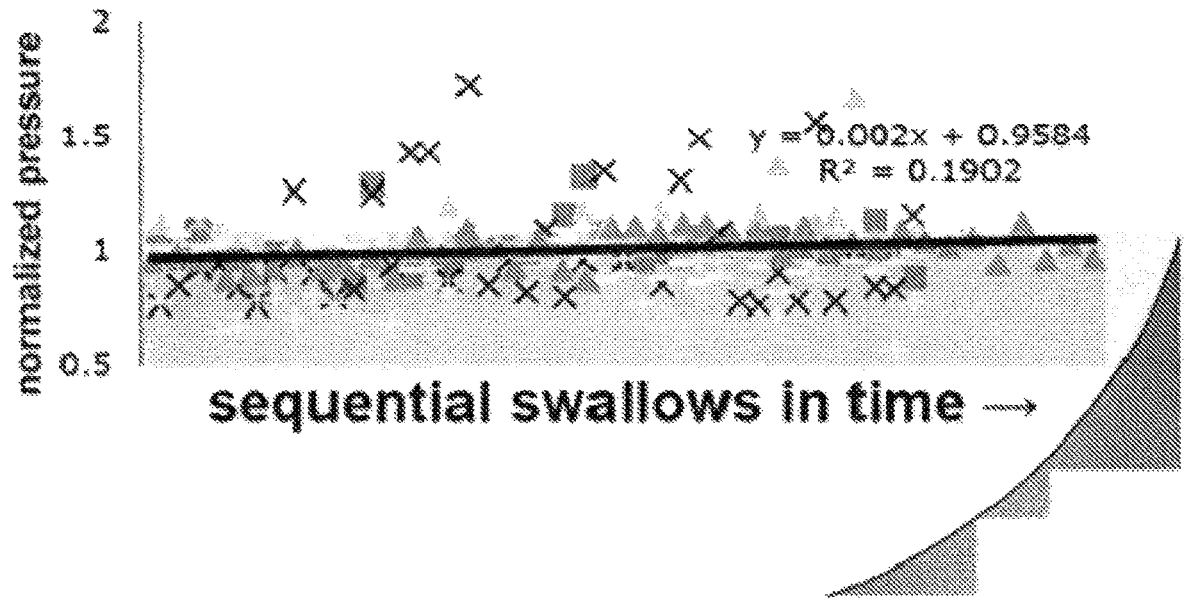
Figure 22:
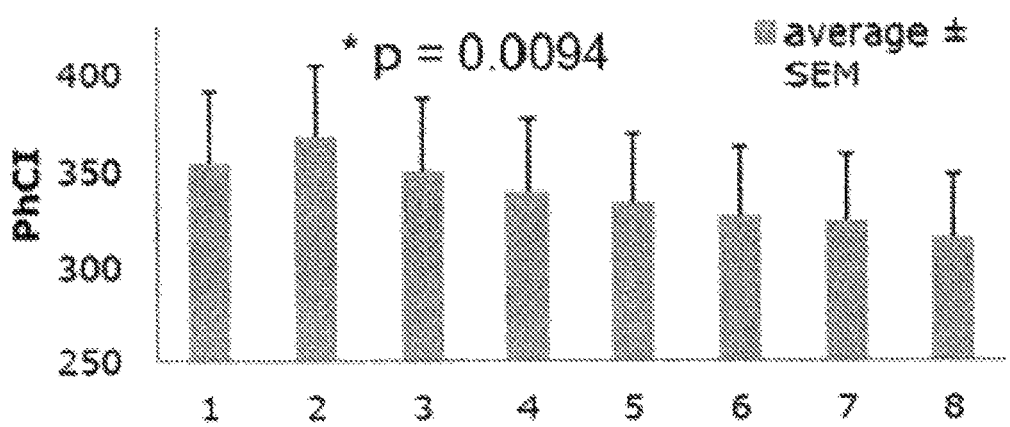
FIG. 22 shows graphs of the effect with and without use of a swallow exerciser device of the invention (referred to as a Resistance Exercise Device (RED) in FIG. 22) on the onset of fatigue.
Figure 22:
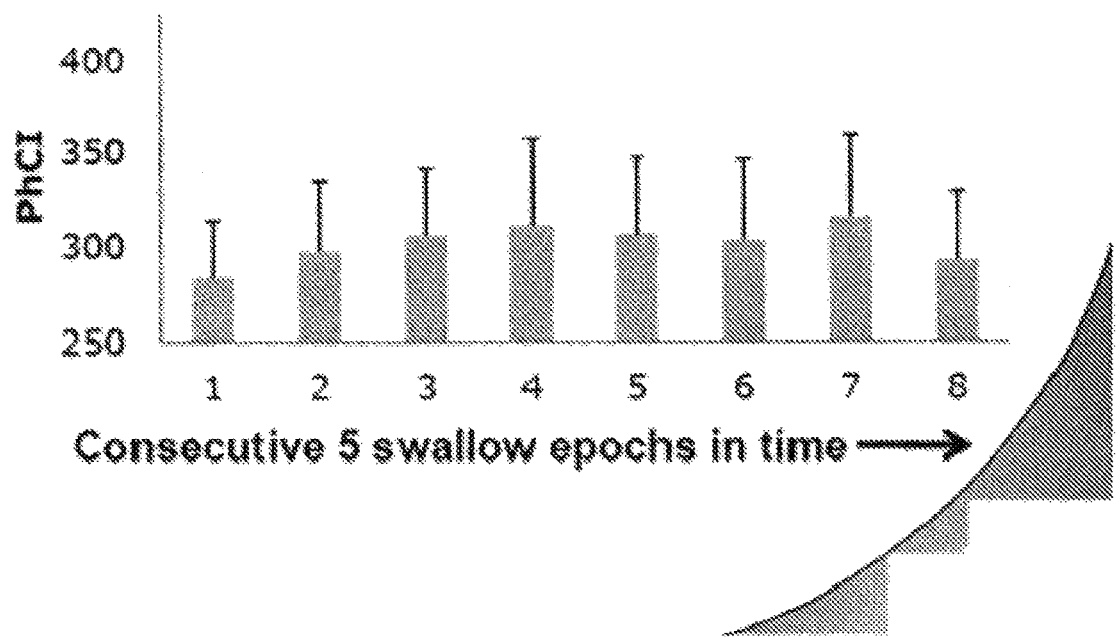

Referring now to FIG. 21, there is shown all subjects data for the recording site 8 centimeters above the upper margin of the PE-HPZ. To fit all data on the same scale, pressure data is normalized to the mean pressure for site 8 centimeters within each subject across each 40 swallow sequence. Individual subject data is represented as different colors and symbols. The regression line represents fitting of the mean data across subjects.

Since PhCI reflects the pressure phenomena across the entire pharynx, further analysis revealed that the fatigue trend significantly affected some but not all of the recording sites. A one sample t-test was used to test to determine whether correlation coefficients are significantly different from zero with the listed probability of Type I error. See Table 1 below.

TABLE 1

| With RED (Sites) | Z scored correlation coefficient | P value |
|---|---|---|
| P2 | 0.07 ± 0.46 | 0.74 |
| P3 | −0.21 ± 0.39 | 0.56 |
| P4 | −0.09 ± 0.31 | 0.27 |
| P5 | −0.17 ± 0.53 | 0.21 |
| P6 | −0.28 ± 0.58 | 0.05 |
| P7 | −0.41 ± 0.59 | 0.03* |
| P8 | −0.56 ± 0.34 | 0.003* |

We analyzed the effect of sham resistance exercise on pharyngeal contraction. Fatigue behavior was not seen in swallow sequences without the exerciser. A one sample t-test was used to test whether correlation coefficients are significantly different from zero with the listed probability of Type I error. See Table 2 below.

TABLE 2

| Without RED (Sites) | Z scored correlation coefficient | P value |
|---|---|---|
| P2 | 0.04 ± 0.38 | 0.94 |
| P3 | −0.11 ± 0.28 | 0.10 |
| P4 | 0.04 ± 0.33 | 0.45 |
| P5 | 0.15 ± 0.32 | 0.45 |
| P6 | 0.14 ± 0.62 | 0.58 |
| P7 | 0.14 ± 0.62 | 0.53 |
| P8 | −0.002 ± 0.42 | 0.64 |

We analyzed the onset of fatigue. A set of 40 swallows was partitioned into 5 swallow epochs. Then, 5 swallows were averaged in each epoch. ANOVA average PhCI was tested across epochs and across all subjects. Significant differences across epochs were seen for PhCI with the RED but not without the RED. Differences were driven by significant difference in epoch 2 compared to epoch 8 (p=0.0115). Epoch-wise tests were corrected for multiple comparisons. See FIG. 22.

We also analyzed the effect of exerciser load of the swallow exerciser device of the invention on the pharyngeal contractile integral (PhCI) with and without use of the swallow exerciser device. See FIG. 23.

Conclusions from Example 3

Swallow against an increased external load induced by a swallow exerciser device of the present disclosure is safe and effective for inducing fatigue in pharyngeal peristalsis and thus can strengthen the pharyngeal constrictor muscles. This finding provides an opportunity for treatment of pharyngeal weakness observed in patients with oro-pharyngeal dysphagia.

Thus, the invention provides a swallow exerciser device that exercises and thereby strengthens the muscles involved in swallowing.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A device for improving swallowing function in a subject, the device comprising:
a rigid shell having a longitudinal dimension such that the shell is configured to extend above a larynx of the subject and below the larynx of the subject, the shell having a distal surface and an opposite proximal surface;
an adjustable fastener dimensioned to secure the shell around a neck of the subject with the shell positioned over the larynx of the subject; and
an inflatable pad coupled to a surface of the shell, wherein the inflatable pad is dimensioned to apply resistance to movement of at least one swallowing muscle of the subject when the shell is positioned over the larynx of the subject and when the inflatable pad is in an inflated position.

2. The device of claim 1 wherein:
the adjustable fastener is connected to the shell.

3. The device of claim 1 further comprising:
a spacer positioned between the shell and the adjustable fastener, the spacer being attached to the shell and/or the adjustable fastener.

4. The device of claim 3 wherein:
the spacer is inwardly spaced from a perimeter edge of the shell.

5. The device of claim 1 wherein:
the inflatable pad is dimensioned to apply resistance to force of at least one muscle of the tongue of the subject when the shell is positioned over the larynx of the subject and when the inflatable pad is in the inflated position.

6. The device of claim 1 wherein:
the inflatable pad is dimensioned to apply resistance to force of at least one suprahyoid muscle of the subject when the shell is positioned over the larynx of the subject and when the inflatable pad is in the inflated position.

7. The device of claim 6 wherein:
the inflatable pad is dimensioned to apply resistance to force of at least one of the digastric muscle, geniohyoid, and mylohyoid of the subject when the shell is positioned over the larynx of the subject and when the inflatable pad is in the inflated position.

8. The device of claim 1 wherein:
the inflatable pad is dimensioned to apply resistance to force of at least one infrahyoid muscle of the subject when the shell is positioned over the larynx of the subject and when the inflatable pad is in the inflated position.

9. The device of claim 1 wherein:
the inflatable pad is dimensioned to apply resistance to force of at least one muscle of a longitudinal muscle group of the subject when the shell is positioned over the larynx of the subject and when the inflatable pad is in the inflated position.

10. The device of claim 9 wherein:
the inflatable pad is dimensioned to apply resistance to force of at least one of the palatopharyngeus, stylopharyngeus and salpingopharyngeus of the subject when the shell is positioned over the larynx of the subject and when the inflatable pad is in the inflated position.

11. The device of claim 1 wherein:
the inflatable pad is dimensioned to apply resistance to force of at least one pharyngeal constrictor muscle of the subject when the shell is positioned over the larynx of the subject and when the inflatable pad is in the inflated position.

12. The device of claim 1 wherein:
the inflatable pad is dimensioned to increase resistance to a flow of swallowed food out of a pharynx of the subject when the shell is positioned over the larynx of the subject and when the inflatable pad is in the inflated position.

13. The device of claim 1 wherein:
the inflatable pad is dimensioned to apply resistance to superior and anterior movement of the larynx of the subject when the shell is positioned over the larynx of the subject and when the inflatable pad is in the inflated position.

14. The device of claim 1 wherein:
the inflatable pad is dimensioned to apply resistance to superior movement of a hyoid bone of the subject when the shell is positioned over the larynx of the subject and when the inflatable pad is in the inflated position.

15. The device of claim 1 wherein:
the inflatable pad is dimensioned to avoid applying pressure to a carotid artery of the subject when the shell is positioned over the larynx of the subject and when the inflatable pad is in the inflated position.

16. The device of claim 1 wherein:
the inflatable pad is dimensioned to avoid applying pressure to a jugular vein of the subject when the shell is positioned over the larynx of the subject and when the inflatable pad is in the inflated position.

17. The device of claim 1 wherein:
a transverse cross-section of the proximal surface of the shell is concave.

18. The device of claim 1 wherein:
a transverse cross-section of the proximal surface of the shell taken along a transverse axis of the shell is concave along an entire length of the transverse cross-section.

19. The device of claim 1 wherein:
a longitudinal cross-section of the proximal surface of the shell is concave.

20. The device of claim 1 wherein:
a longitudinal cross-section of the proximal surface of the shell taken along a longitudinal axis of the shell is concave along an entire length of the longitudinal cross-section.

21. The device of claim 1 wherein:
a transverse cross-section of the proximal surface of the shell is concave,
a longitudinal cross-section of the proximal surface of the shell is concave, and
the longitudinal cross-section of the proximal surface is less concave than the transverse cross-section of the proximal surface.

22. The device of claim 1 wherein:
the shell is dimensioned to secure the shell around the neck of the subject such that the shell extends from cricoid cartilage to thyroid cartilage of the subject along a longitudinal axis of the shell.

23. The device of claim 1 wherein:
the shell is dimensioned to secure the shell around the neck of the subject such that the shell extends from cricoid cartilage to above a hyoid bone of the subject along a longitudinal axis of the shell.

24. The device of claim 1 wherein:
the surface of the shell includes an indentation for receiving the inflatable pad.

25. The device of claim 1 further comprising:
a viscoelastic layer attached to a proximal side of the inflatable pad.

26. The device of claim 25 wherein:
the viscoelastic layer comprises a shape memory foam.

27. The device of claim 25 further comprising:
a proximal layer covering a proximal side of the viscoelastic layer.

28. The device of claim 27 wherein:
the proximal layer comprises a fabric.

29. The device of claim 1 wherein:
the device does not trigger swallowing in the subject.

30. The device of claim 1 wherein:
the device does not include a vibrating element.

31. The device of claim 1 wherein:
the device does not include an electrical element.

32. The device of claim 1 wherein:
the adjustable fastener includes a hook-type fastener component and a loop-type fastener component.

33. The device of claim 1 further comprising:
an inflation apparatus for inflating and deflating the inflatable pad, the inflation apparatus including a pump for inflating the inflatable pad, a conduit in fluid communication with the inflatable pad and the pump, and a valve for regulating inflation and deflation of the inflatable pad.

34. The device of claim 33 wherein:
the inflation apparatus further comprises a gage for measuring a pressure level in the inflatable pad.

35. The device of claim 1 wherein:
the inflatable pad has a first surface and an opposite second surface, the first surface being connected to the distal surface of the shell and the second surface being configured to face the neck of the subject when the shell is positioned over the larynx of the subject.

36. The device of claim 1 wherein:
the distal surface of the shell defines an internal volume of the shell, and the inflatable pad is received within the internal volume of the shell.

37. The device of claim 1, wherein:
the shell has a transverse dimension taken along a transverse axis (T) of about 2 to about 5 centimeters.

* * * * *